US009353390B2

(12) United States Patent
Yan et al.

(10) Patent No.: US 9,353,390 B2
(45) Date of Patent: May 31, 2016

(54) GENETICALLY ENGINEERED MICROBES AND METHODS FOR PRODUCING 4-HYDROXYCOUMARIN

(71) Applicant: University of Georgia Research Foundation, Inc., Athens, GA (US)

(72) Inventors: Yajun Yan, Athens, GA (US); Yuheng Lin, Marietta, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 14/304,105

(22) Filed: Jun. 13, 2014

(65) Prior Publication Data

US 2014/0370557 A1  Dec. 18, 2014

Related U.S. Application Data

(60) Provisional application No. 61/834,546, filed on Jun. 13, 2013.

(51) Int. Cl.
| | | |
|---|---|---|
| C12P 17/06 | (2006.01) | |
| C07D 311/46 | (2006.01) | |
| C07D 311/56 | (2006.01) | |
| C12N 15/52 | (2006.01) | |

(52) U.S. Cl.
CPC .............. *C12P 17/06* (2013.01); *C07D 311/46* (2013.01); *C07D 311/56* (2013.01); *C12N 15/52* (2013.01)

(58) Field of Classification Search
None
See application file for complete search history.

(56) References Cited

U.S. PATENT DOCUMENTS

| | | | |
|---|---|---|---|
| 4,703,004 A | 10/1987 | Hopp et al. | |
| 4,782,137 A | 11/1988 | Hopp et al. | |
| 5,594,115 A | 1/1997 | Sharma | |
| 5,935,824 A | 8/1999 | Sgarlato | |

OTHER PUBLICATIONS

National Center for Biotechnology Information, National Library of Medicine, National Institutes of Health, GenBank Locus BAC78380, Accession No. BAC78380, "putative salicyl-AMP ligase [*Streptomyces* sp. WA46]," [online]. Bethesda, MD [retrieved on Aug. 3, 2015]. Retrieved from the Internet: <URL: http://www.ncbi.nlm.nih.gov/protein/BAC78380.1>; 2 pgs.
National Center for Biotechnology Information, National Library of Medicine, National Institutes of Health, GenBank Locus NP_249690, Accession No. NP_249690, "2-heptyl-4(1H)-quinolone synthase PqsD [Pseudomonas aeruginosa PAO1]," [online]. Bethesda, MD [retrieved on Aug. 3, 2015]. Retrieved from the Internet: <URL: http://www.ncbi.nlm.nih.gov/protein/NP_249690.1>; 3 pgs.
National Center for Biotechnology Information, National Library of Medicine, National Institutes of Health, GenBank Locus NP_252920, Accession No. NP_252920, "isochorismate-pyruvate lyase [Pseudomonas aeruginosa PAO1]," [online]. Bethesda, MD [retrieved on Aug. 3, 2015]. Retrieved from the Internet: <URL: http://www.ncbi.nlm.nih.gov/protein/NP_252920.1>; 3 pgs.
National Center for Biotechnology Information, National Library of Medicine, National Institutes of Health, GenBank Locus NP_415125, Accession No. NP_415125, "isochorismate synthase 1 [*Escherichia coli* str. K-12 substr. MG1655]," [online]. Bethesda, MD [retrieved on Aug. 3, 2015]. Retrieved from the Internet: <URL: http://www.ncbi.nlm.nih.gov/protein/NP_415125.1.>; 3 pgs.
Ajikumar et al. "Isoprenoid Pathway Optimization for Taxol Precursor Overproduction in *Escherichia coli*" *Science*, Oct. 1, 2010; 330(6000):70-4.
Anthony et al. "Optimization of the mevalonate-based isoprenoid biosynthetic pathway in *Escherichia coli* for production of the antimalarial drug precursor amorpha-4,11-diene" *Metab. Eng.* Jan. 2009; 11(1):13-9. Epub Aug. 12, 2008.
Atsumi et al. "Non-fermentative pathways for synthesis of branched-chain higher alcohols as biofuels" *Nature*, Jan. 3, 2008; 451(7174):86-9.
Beinema et al. "Pharmacogenetic differences between warfarin, acenocoumarol and phenprocoumon" *Thromb. Haemos.*, Dec. 2008; 100(6):1052-7.
Bera et al. "Structure of PqsD, a Pseudomonas quinolone signal biosynthetic enzyme, in complex with anthranilate" *Biochemistry (Mosc.)* Sep. 15, 2009; 48(36):8644-55.
Beuerle et al., "Purification and characterization of benzoate:coenzyme A ligase from *Clarkia breweri*" *Arch. Biochem. Biophys.* 2002; 400(2):258-64.
Bond-Watts et al. "Enzyme mechanism as a kinetic control element for designing synthetic biofuel pathways" *Nat. Chem. Biol.* Apr. 2011; 7(4):222-7.
Bye et al. "The biosynthesis of 4-hydroxycoumarin and dicoumarol by *Aspergillus fumigatus* Fresenius" *Biochem. J.* 1970; 117(2):237-45.
Chen et al. "Biosynthesis of salicylic acid in plants" *Plant Signal Behav.* 2009; 4(6):493-6. Epub Jun. 12, 2009.
Cohen et al. "Venous thromboembolism (VTE) in Europe. The number of VTE events and associated morbidity and mortality" *Thromb. Haemost.* 2007; 98(4):756-64.
Daruwala et al., "Menaquinone (vitamin K2) biosynthesis: overexpression, purification, and characterization of a new isochorismate synthase from *Escherichia coli*" *J. Bacteriol.* 1997; 179(10), 3133-8.
Dhamankar et al. "Microbial chemical factories: recent advances in pathway engineering for synthesis of value added chemicals" *Curr. Opin. Struct. Biol.* Aug. 2011; 21(4):488-94.

(Continued)

*Primary Examiner* — Nashaat Nashed
(74) *Attorney, Agent, or Firm* — Mueting, Raasch & Gebhardt, P.A.

(57) ABSTRACT

Provided herein are methods for the biosynthesis of 4-hydroxycoumarin. In one embodiment, provided herein are genetically engineered microbes that include a metabolic pathway for the production of 4-hydroxycoumarin. Also provided are methods for using the genetically engineered microbes to produce 4-hydroxycoumarin, and using the 4-hydroxycoumarin as the starting point for the synthesis of other compounds.

19 Claims, 17 Drawing Sheets

(56) References Cited

OTHER PUBLICATIONS

Gaille et al. "Salicylate biosynthesis in *Pseudomonas aeruginosa*. Purification and characterization of PchB, a novel bifunctional enzyme displaying isochorismate pyruvate-lyase and chorismate mutase activities" *J. Biol. Chem.* 2002; 277(24):21768-75.
Gao et al. "Clean and Convenient One-Pot Synthesis of 4-Hydroxycoumarin and 4-Hydroxy-2-Quinolinone Derivatives" *Synthetic Commun.* 2010; 40:732-8.
Geissler et al., "Purification and properties of benzoate-coenzyme A ligase, a *Rhodopseudomonas palustris* enzyme involved in the anaerobic degradation of benzoate" *J. Bacteriol.* 1988;170(4):1709-14.
Gerhardt et al., *Methods for General and Molecular Bacteriology*, American Society for Microbiology: Washington D.C.; 1994. Cover page, title page, and table of contents, and Chapters 13-14 and 16-18.
Gibson et al. "Enzymatic assembly of DNA molecules up to several hundred kilobases" *Nat. Methods*, 2009; 6(5):343-5.
Heeb et al. "Quinolones: from antibiotics to autoinducers" *FEMS Microbiol. Rev.* 2011; 35(2):247-74.
Heit et al., "Estimated annual number of incident and recurrent, non-fatal and fatal venous thromboembolism (VTE) events in the US" *Blood* 106, 267a-267a (2005).
Huo et al., "Conversion of proteins into biofuels by engineering nitrogen flux" *Nat. Biotechnol.*, 2011; 29(4):346-51.
Ishiyama et al., "Novel pathway of salicylate degradation by *Streptomyces* sp. strain WA46" *Appl. Environ. Microbiol.* 2004; 70(3):1297-306.
Ivanov et al. "New Efficient Catalysts in the Synthesis of Warfarin and Acenocoumarol" *Arch. Pharm. (Weinheim)* 1990; 323(8):521-2.
Jossek et al., "Characterization of a new feedback-resistant 3-deoxy-D-arabino-heptulosonate 7-phosphate synthase AroF of *Escherichia coli*" FEMS Microbiol Lett., 2001; 202:145-8.
Kai et al. "Scopoletin is biosynthesized via *ortho*-hydroxylation of feruloyl CoA by a 2-oxoglutarate-dependent dioxygenase in *Arabidopsis thaliana*" *Plant J.* 2008; 55(6):989-9.
Kikuchi et al. "Mutational analysis of the feedback sites of phenylalanine-sensitive 3-deoxy-D-arabino-heptulosonate-7-phosphate synthase of *Escherichia coli*" *Appl. Environ. Microbiol.* 1997; 63(2):761-2.
Leonard et al. "Engineering central metabolic pathways for high-level flavonoid production in *Escherichia coli*" *Appl. Environ. Microbiol.* 2007; 73(12):3877-86.
Lequesne et al., "The Natural Coumarins—Occurrence, Chemistry and Biochemistry" *J. Am. Chem. Soc.* 1983; 105:6536.
Li et al., "Bioprospecting metagenomes: glycosyl hydrolases for converting biomass" Biotechnol Biofuels, May 18, 2009; 2:10.
Lim et al. "High-Yield Resveratrol Production in Engineered *Escherichia coli*" *Appl. Environ. Microbiol.* 2011; 77(10):3451-60.
Lin et al. "Biosynthesis of caffeic acid in *Escherichia coli* using its endogenous hydroxylase complex" *Microb. Cell. Fact.* Apr. 4, 2012; 11:42, 9 pages.
Ling, et al., "Enediyne antitumor antibiotic maduropeptin biosynthesis featuring a C-methyltransferase that acts on a CoA-tethered aromatic substrate" *J. Am. Chem. Soc.* 2010; 132(36):12534-6.
Liu et al., "Overexpression, purification, and characterization of isochorismate synthase (EntC), the first enzyme involved in the biosynthesis of enterobactin from chorismate" *Biochemistry (Mosc.)* 1990; 29(6):1417-25.
Liu et al. "A novel 4-hydroxycoumarin biosynthetic pathway" *Plant Mol. Biol.* 2010; 72(1-2):17-25.
Lütke-Eversloh et al. "L-tyrosine production by deregulated strains of *Escherichia coli*" *Appl. Microbiol. Biotechnol.* 2007; 75(1):103-10.
Lütke-Eversloh et al. "Combinatorial pathway analysis for improved L-tyrosine production in *Escherichia coli*: Identification of enzymatic bottlenecks by systematic gene overexpression" *Metab. Eng.* 2008; 10(2):69-77.
Martin et al., "Engineering a mevalonate pathway in *Escherichia coli* for production of terpenoids" *Nat. Biotechnol.* 2003; 21(7):796-802.

Matsumoto et al. "Molecular cloning and functional analysis of the *ortho*-hydroxylases of *p*-coumaroyl coenzyme A/feruloyl coenzyme A involved in formation of umbelliferone and scopoletin in sweet potato, *Ipomoea batatas* (L.) Lam." *Phytochemistry*, Feb. 2012; 74:49-57.
Melnikova, "The anticoagulants market" *Nat. Rev. Drug Discov.* 2009; 8(5):353-4.
Murray et al., *Natural Coumarins: occurrence, chemistry and biochemistry*, John Wiley & Sons Ltd., Chichester, New York; 1982. Cover page, title page and table of contents.
Nagachar et al. "Roles of *trpE2*, *entC* and *entD* in salicylic acid biosynthesis in *Mycobacterium smegmatis*" FEMS Microbiol. Lett. 2010; 308(2):159-65.
Nakagawa et al. "A bacterial platform for fermentative production of plant alkaloids" *Nat. Commun.* 2011; 2:326. 8 pages.
Payne et al. "Synthesis and evaluation of 2,5-dihydrochorismate analogues as inhibitors of the chorismate-utilising enzymes" *Org. Biomol. Chem.* 2009; 7(11):2421-9.
Pickens et al., "Biochemical analysis of the biosynthetic pathway of an anticancer tetracycline SF2575" *J. Am. Chem. Soc.* 2009; 131(48):17677-89.
Ray et al., "Mutational analysis of the catalytic and feedback sites of the tryptophan-sensitive 3-deoxy-D-arabino-heptulosonate-7-phosphate synthase of *Escherichia coli*" J. Bacteriol., 1988; 170:5500-6.
Ro et al. "Production of the antimalarial drug precursor artemisinic acid in engineered yeast" *Nature*, 2006;440(7086):940-3.
Rogozinska et al. "Efficient "on water" organocatalytic protocol for the synthesis of optically pure warfarin anticoagulant" *Green Chem.* 2011; 13:1155-7.
Rueping et al. "A review of new developments in the Friedel-Crafts alkylation—From green chemistry to asymmetric catalysis" *Beilstein J. Org. Chem.* 2010; 6:6. 24 pages.
Solis et al. "Automated design of synthetic ribosome binding sites to control protein expression" *Nat. Biotechnol.* 2009; 27(10): 946-50.
Sambrook et al, *Molecular Cloning: A Laboratory Manual.*, Cold Spring Harbor Laboratory Press, Cold Spring Harbor, New York, 2012. Cover page, title page, table of contents. 34 pages.
Santos et al. "Optimization of a heterologous pathway for the production of flavonoids from glucose" *Metab. Eng.* 2011; 13(4):392-400.
Serino et al., "Structural genes for salicylate biosynthesis from chorismate in Pseudomonas aeruginosa" *Mol. Gen. Genet.* 1995; 249(2):217-28.
Shen et al. "Driving forces enable high-titer anaerobic 1-butanol synthesis in *Escherichia coli*" *Appl. Environ. Microbiol.* 2011; 77(9):2905-15.
Tatusova et al., "BLAST 2 Sequences, a new tool for comparing protein and nucleotide sequences" *FEMS Microbiol Lett*, 1999; 174(2):247-50.
Vialart et al. "A 2-oxoglutarate-dependent dioxygenase from *Ruta graveolens* L. exhibits *p*-coumaroyl CoA 2'-hydroxylase activity (C2'H): a missing step in the synthesis of umbelliferone in plants" *Plant J.* May 2012; 70(3):460-70.
Xu et al. "Modular optimization of multi-gene pathways for fatty acids production in *E. coli.*" *Nat. Commun.* 2013; 4:1409.
Yan et al. "High-yield anthocyanin biosynthesis in engineered *Escherichia coli.*" *Biotechnol. Bioeng.* 2008; 100(1):126-40.
Zha et al. "Improving cellular malonyl-CoA level in *Escherichia coli* via metabolic engineering" *Metab. Eng.* 2009; 11(3):192-8.
Zhang et al., "PqsD is responsible for the synthesis of 2,4-dihydroxyquinoline, an extracellular metabolite produced by *Pseudomonas aeruginosa*" *J. Biol. Chem.* 2008; 283(43):28788-94.
Zhang et al. "Design of a dynamic sensor-regulator system for production of chemicals and fuels derived from fatty acids" *Nat. Biotechnol.* Mar. 25, 2012; 30(4):354-9.
Lin et al, "Microbial Biosynthesis of the Anticoagulant Precursor 4-Hydroxycoumarin", *Nature Communications*, Accepted Sep. 12, 2013, published Oct. 16, 2013, pp. 1-8.
Lin et al, "Microbial Biosynthesis of the Anticoagulant Precursor 4-Hydroxycoumarin", *Nature Communications*, Accepted Sep. 12, 2013, published Oct. 16, 2013, Supplementary Information, 19 pages.

SEQ ID NO:1
MDTSLAEEVQQTMATLAPNRFFFMSPYRSFTTSGCFARFDEPAVNGDSPDSPFQQKLAALFADAKAQGIKNPVM
VGAIPFDPRQPSSLYIPESWQSFSRQEKQASARRFTRSQSLNVVERQAIPEQTTFEQMVARAAALTATPQVDKV
VLSRLIDITTDAAIDSGVLLERLIAQNPVSYNFHVPLADGGVLLGASPELLLRKDGERFSSIPLAGSARRQPDE
VLDREAGNRLLASEKDRHEHELVTQAMKEVLRERSSELHVPSSPQLTTTPTLWHLATPFEGKANSQENALTLAC
LLHPTPALSGFPHQAATQVIAELEPFDRELFGGIVGWCDSEGNGEWVVTIRCAKLRENQVRLFAGAGIVPASSP
LGEWRETGVKLSTMLNVFGLH

SEQ ID NO:2
MKTPEDCTGLADIREAIDRIDLDIVQALGRRMDYVKAASRFKASEAAIPAPERVAAMLPERARWAEENGLDAPF
VEGLFAQIIHWYIAEQIKYWRQTRGAA

SEQ ID NO:3
MTREGFVPWPKEAADRYREAGYWRGRPLGSYLHEWAETYGDTVAVVDGDTRLTYRQLVDRADGLACRLLDSGLN
PGDAMLVQLPNGWEFVTLTLACLRAGIAPVMAMPAHRGHELRYLAAHAEVTSIAVPDRLGDFDHQALGREVAED
TPSVGLLLVAGGTVGTDATDLRALAEPADDPVTARARLDRIAPDSGDIAVFLLSGGTTGLPKLITRTHDDYEYN
ARRSAEVCGLDSDSVYLVALPAGHNFPLACPGILGTLMNGGRVVLARTPEPGKVLPLMAAEGVTATAAVPAVVQ
RWIDAVASGRHPAPPALRLLQVGGARLAPEVARRAEPVLGGTLQQVFGMAEGLLNYTRPDDPDDIKIETQGRPM
CPDDEILVVDASDNPVPPGEMGALLTRGPYTPRGYYRAAEHNARAFTPDGWYRTGDVVRLHPSGNLVVEGRDKD
LINRGGEKISAEEVENLIYRLPGVARVAAVAKADPDLGERVCAVVVVEPGTQLSLESVRAALTAMQVARYKLPE
DLLVVDELPLTKVGKIDKKRLRDVVRGKADSVEAV

SEQ ID NO:4
MGNPILAGLGFSLPKRQVSNHDLVGRINTSDEFIVERTGVRTRYHVEPEQAVSALMVPAARQAIEAAGLLPEDI
DLLLVNTLSPDHHDPSQACLIQPLLGLRHIPVLDIRAQCSGLLYGLQMARGQILAGLARHVLVVCGEVLSKRMD
CSDRGRNLSILLGDGAGAVVVSAGESLEDGLLDLRLGADGNYFDLLMTAAPGSASPTFLDENVLREGGGEFLMR
GRPMFEHASQTLVRIAGEMLAAHELTLDDIDHVICHQPNLRILDAVQEQLGIPQHKFAVTVDRLGNMASASTPV
TLAMFWPDIQPGQRVLVLTYGSGATWGAALYRKPEEVNRPC

GENETICALLY ENGINEERED MICROBES AND METHODS FOR PRODUCING 4-HYDROXYCOUMARIN

CROSS-REFERENCE TO RELATED APPLICATIONS

This application claims the benefit of U.S. Provisional Application Ser. No. 61/834,546, filed Jun. 13, 2013, which is incorporated by reference herein.

SEQUENCE LISTING

This application contains a Sequence Listing electronically submitted via EFS-Web to the United States Patent and Trademark Office as an ASCII text file entitled "US14304105_SequenceListing_ST25.txt" having a size of 23 kilobytes and created on Aug. 6, 2014. The information contained in the Sequence Listing is incorporated by reference herein.

BACKGROUND

Thromboembolic diseases including venous thromboembolism (VTE) and arterial thrombosis are a leading cause of patient morbidity and mortality worldwide. Annually, VTE alone results in approximately 300,000 and 550,000 deaths in the US and Europe, respectively, and an even larger number of non-fatal events (Heit et al., *Blood* 106, 267a-267a (2005), (Cohen et al. *Thromb. Haemost.* 98, 756-764 (2007). 4-Hydroxycoumarin (4HC) type oral anticoagulant drugs have been playing significant roles against thromboembolic diseases. Interestingly, anticoagulant function of 4HC derivatives was initially discovered due to its cause of a fetal animal disease manifesting as internal bleeding of the livestock fed with moldy sweet clover forage (called "sweet clover disease"). Indeed, fermentation of plant materials containing melilotoside by molds causes the formation of 4HC and its derivative dicoumarol. The latter demonstrates the blood anticoagulant property by antagonism of vitamin K and acted as a forerunner of the synthetic anticoagulants typified by warfarin (Murray, R. D. H., Méndez, J. & Brown, S. A. *Wiley, Chichester* (1982). Warfarin is one of the most prescribed oral anticoagulants worldwide with a $300 million global market in 2008 (Melnikova, I. *Nat. Rev. Drug Discov.* 8, 353-354 (2009)). Besides, acenocoumarol and phenprocoumon are commonly administered in Europe (Beinema et al. *Thromb. Haemost.* 100, 1052-1057 (2008)). These drugs share the 4HC core structure but differ in 3-substitution on the pyrone ring, and can be chemically synthesized using 4HC as an immediate precursor (Ivanov et al. *Arch. Pharm. (Weinheim)* 323, 521-522 (1990)), (Rueping et al. *Beilstein J. Org. Chem.* 6, 6 (2010)).

In past decades, various strategies were developed to chemically synthesize 4HC using petro-derived chemicals, such as phenol, acetosalicylate, methylsalicylate, or 2'-hydroxyacetophenone as starting materials (Gao et al. *Synthetic Commun.* 40, 732-738 (2010)). Nevertheless, increasing concerns on petroleum depletion and environmental issues have stimulated greater efforts towards the development of biological processes utilizing renewable resources instead of petro-based chemicals. The convergence of genetics, bioinformatics, and metabolic engineering greatly promoted the engineered biosynthesis of a variety of pharmaceutically important compounds in heterologous microbial hosts, e.g. artemisinic acid (Ro., et al. *Nature* 440, 940-943 (2006)), taxadiene (Ajikumar et al. *Science* 330, 70-74 (2010)), caffeic acid (Lin et al. *Microb. Cell. Fact.* 11, 42 (2012), benzylisoquinoline alkaloids (Nakagawa et al. *Nat. Commun.* 2 (2011)), terpenoids (Martin et al. *Nat. Biotechnol.* 21, 796-802 (2003)), anthocyanin (Yan et al. *Biotechnol. Bioeng.* 100, 126-140 (2008)), flavonoids (Santos et al. *Metab. Eng.* 13, 392-400 (2011)), and resveratrol (Lim et al. *Appl. Environ. Microbiol.* 77, 3451-3460 (2011)). All these successful cases were built on thorough understanding of the products' native biosynthetic mechanisms, especially genetic and biochemical properties of the involved enzymes. However, lack of knowledge in these aspects hindered the reconstitution of the biosynthesis of pharmaceutically important 4HC. Although it was proposed that 4HC was formed when melilotoside-containing plant materials were fermented by molds and a biosynthetic scheme was described by isotopic labeling analysis (Lequesne, P. W., *J. Am. Chem. Soc.* 105, 6536-6536 (1983)), involved enzymes have not been identified (Bye et al. *Biochem. J.* 117, 237-245 (1970)). Several recent studies revealed that the ortho-hydroxylated cinnamoyl-CoA analogs can form coumarins by spontaneous trans/cis isomerization and lactonization (Kai et al. *Plant J.* 55, 989-999 (2008)), (Vialart et al. *Plant J.* 70, 460-470 (2012)), (Matsumoto et al. *Phytochemistry* 74, 49-57 (2012)), suggesting that the pathway might be shunted from trans-2-coumaroyl-CoA to generate coumarin rather than 4HC. Recently, Liu et al identified several biphenyl synthases (BISs) from *Sorbus aucuparia* that catalyze the formation of 3,5-dihydroxybiphenyl through decarboxylative condensation of three malonyl-CoA molecules with benzoyl-CoA. Surprisingly, when ortho-hydroxybenzoyl-CoA (salicoyl-CoA) was used in place of benzoyl-CoA as a substrate, only one molecule of malonyl-CoA was condensed to form 4HC, suggesting that the ortho-hydroxyl group facilitates the intramolecular cyclization without the condensation of another two malonyl-CoA molecules. Accordingly, a biosynthetic pathway extended from plant salicylate biosynthesis was proposed (Liu et al. *Plant Mol. Biol.* 72, 17-25 (2010)). However, the same study reported that *S. aucuparia* cells cannot produce 4HC natively even with the presence of supplemented salicylate (Liu et al. *Plant Mol. Biol.* 72, 17-25 (2010)), indicating the absence of a CoA ligase that can convert salicylate to salicoyl-CoA. In addition, salicylate biosynthesis in plants has not been fully elucidated (Chen et al. *Plant Signal Behav.* 4, 493-496 (2009)).

SUMMARY OF THE APPLICATION

Presented herein is the design and constitution of a novel biosynthetic mechanism affording the de novo biosynthesis of 4HC. Remarkably, a FabH-like quinolone synthase was identified by function-based bioprospecting which eliminated the bottleneck of the biosynthetic mechanism. Preliminary optimization via metabolic engineering demonstrated its scale-up potential, leading to efficient biosynthesis of 4HC and in situ semi-synthesis of warfarin. The methods described herein may also be used to produce other compounds for which 4HC is a precursor.

Provided herein are genetically engineered microbes. In one embodiment, a genetically engineered microbe includes a metabolic pathway for the production of 4-hydroxycoumarin from a chorismate intermediate. The microbe, which may be *E. coli*, may be engineered to express an exogenous isochorismate synthase, an isochorismate pyruvate lyase, a salicylate:CoA ligase, a 4HC-forming protein, or a combination thereof. In one embodiment, the 4HC-forming protein is a FabH-like quinolone synthase.

In one embodiment, the genetically engineered microbe includes a first plasmid including a polynucleotide encoding at least one enzyme of the metabolic pathway, where the enzyme is selected from the group consisting of an isochorismate synthase, an isochorismate pyruvate lyase, a salicylate:CoA ligase, and a 4HC-forming protein. In one embodiment, the genetically engineered microbe includes a first plasmid including a polynucleotide encoding an isochorismate synthase and an isochorismate pyruvate lyase, and the microbe further includes a second plasmid including a polynucleotide encoding a salicylate:CoA ligase and a 4HC-forming protein.

In one embodiment, the genetically engineered microbe further includes increased production of chorismate compared to a control cell. In one embodiment, the genetically engineered microbe may be further modified to express a feedback inhibition resistant 3-deoxy-D-arabino-heptulosonate-7-phosphate synthase, such as aroG$^{fbr}$, a phosphoenolpyruvate synthase, a transketolase, a shikimate kinase, or a combination thereof, at an increased level compared to a control cell.

Also provided are methods of using the metabolic pathway described herein. In one embodiment, the method includes culturing a genetically engineered microbe described herein under conditions suitable for the production of 4-hydroxycoumarin. In one embodiment, the method may further include enriching the 4-hydroxycoumarin, for instance by removing the cells from the culture. In one embodiment, the method may further include isolating the 4-hydroxycoumarin. In one embodiment, the method may further include converting the 4-hydroxycoumarin to another compound, such as warfarin, for instance by the addition of benzyldeneacetone and (S,S)-1,2-diphenylethylenediamine to convert the 4-hydroxycoumarin to warfarin.

As used herein, the term "protein" refers broadly to a polymer of two or more amino acids joined together by peptide bonds. The term "protein" also includes molecules which contain more than one polypeptide joined by a disulfide bond, or complexes of proteins that are joined together, covalently or noncovalently, as multimers (e.g., dimers, tetramers). Thus, the terms peptide, oligopeptide, and polypeptide are all included within the definition of protein and these terms are used interchangeably.

As used herein, a protein may be "structurally similar" to a reference protein if the amino acid sequence of the protein possesses a specified amount of sequence similarity and/or sequence identity compared to the reference protein. Thus, a protein may be "structurally similar" to a reference protein if, compared to the reference protein, it possesses a sufficient level of amino acid sequence identity, amino acid sequence similarity, or a combination thereof.

As used herein, the term "polynucleotide" refers to a polymeric form of nucleotides of any length, either ribonucleotides, deoxynucleotides, peptide nucleic acids, or a combination thereof, and includes both single-stranded molecules and double-stranded duplexes. A polynucleotide can be obtained directly from a natural source, or can be prepared with the aid of recombinant, enzymatic, or chemical techniques. In one embodiment, a polynucleotide is isolated.

As used herein, the term "enriched," means that the amount of a substance relative to the amount of one or more contaminants has been increased at least 2 fold, at least 5 fold, at least 10 fold, or at least 15 fold. Enrichment does not imply that all contaminants have been removed. As used herein, an "isolated" substance is one that has been removed from a cell and many of the polypeptides, nucleic acids, and other cellular material of its natural environment are no longer present. A substance may be purified, i.e., at least 60% free, at least 75% free, or at least 90% free from other components with which they are naturally associated. Proteins and polynucleotides that are produced by recombinant, enzymatic, or chemical techniques are considered to be isolated and purified by definition, since they were never present in a cell. For instance, a protein, a polynucleotide, or 4-hydroxycoumarin can be enriched, isolated, or purified.

A "regulatory sequence" is a nucleotide sequence that regulates expression of a coding sequence to which it is operably linked. Nonlimiting examples of regulatory sequences include promoters, enhancers, transcription initiation sites, translation start sites, translation stop sites, transcription terminators, and poly(A) signals. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

As used herein, the term "exogenous protein" and "exogenous polynucleotide" refer to a protein or polynucleotide, respectively, which is not normally or naturally found in a microbe. As used herein, the terms "endogenous protein" and "endogenous polynucleotide" refer to a protein or polynucleotide that is normally or naturally found in a cell microbe. An "endogenous polynucleotide" is also referred to as a "native polynucleotide."

As used herein, "control" cell refers to a cell that is the same species as an engineered cell, but does not has include the same modification as the engineered cell.

Conditions that are "suitable" for an event to occur, or "suitable" conditions are conditions that do not prevent such events from occurring. Thus, these conditions permit, enhance, facilitate, and/or are conducive to the event.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 17. Amino acid sequence of SEQ ID NO:1 (an isochorismate synthase), SEQ ID NO:2 (an isochorismate pyruvate lyase), SEQ ID NO:3 (a salicylate:CoA ligase), and SEQ ID NO:4 (a 4HC-forming enzyme).

DETAILED DESCRIPTION OF ILLUSTRATIVE EMBODIMENTS

Figure 2:
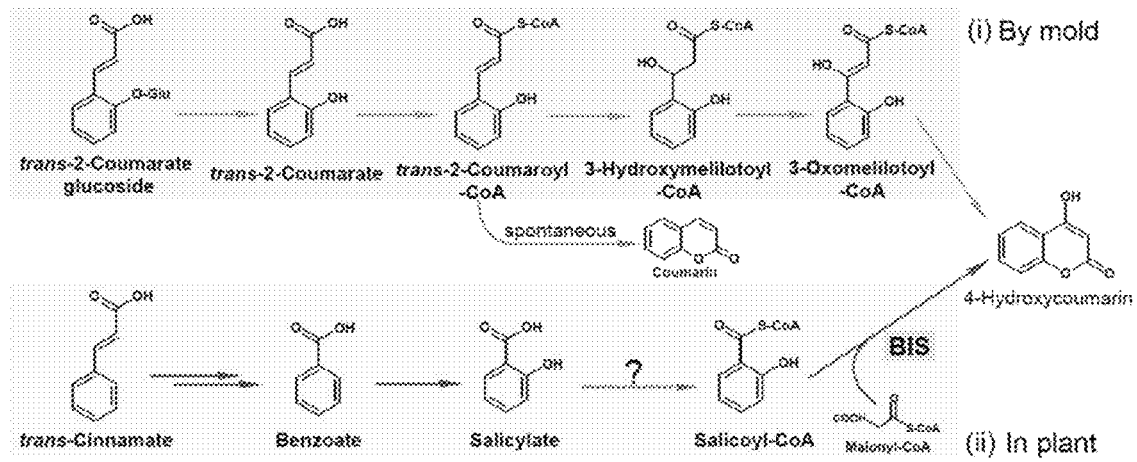
FIG. 2. Schematic representations of natural and artificial 4HC biosynthetic pathways. (A) Previously proposed natural 4HC biosynthetic routes. Scheme i describes the mold-mediated 4HC biosynthesis; scheme ii represents a proposed microbe-independent pathway in plant. Question mark indicates a questionable catalytic step that was not identified. (B) The artificial 4HC biosynthetic mechanism designed in this study. Arrows depicting reactions catalyzed by ICS, IPL, SCL, and BIS, including the production of PYR, CoA, and $CO_2$, and consumption of Coa and Malonyl-CoA indicate non-native catalytic steps; all other arrows indicate the E. coli endogenous metabolism. Enzymes ICS and IPL are highlighted to represent the lower module ii in FIG. 2(A), and SCL and BIS are highlighted to represent the upper module i in FIG. 2(A). E4P: D-erythrose-4-phosphate; PEP: phosphoenolpyruvate; PYR: pyruvate; AcCoA: acetyl-CoA.
Figure 2:
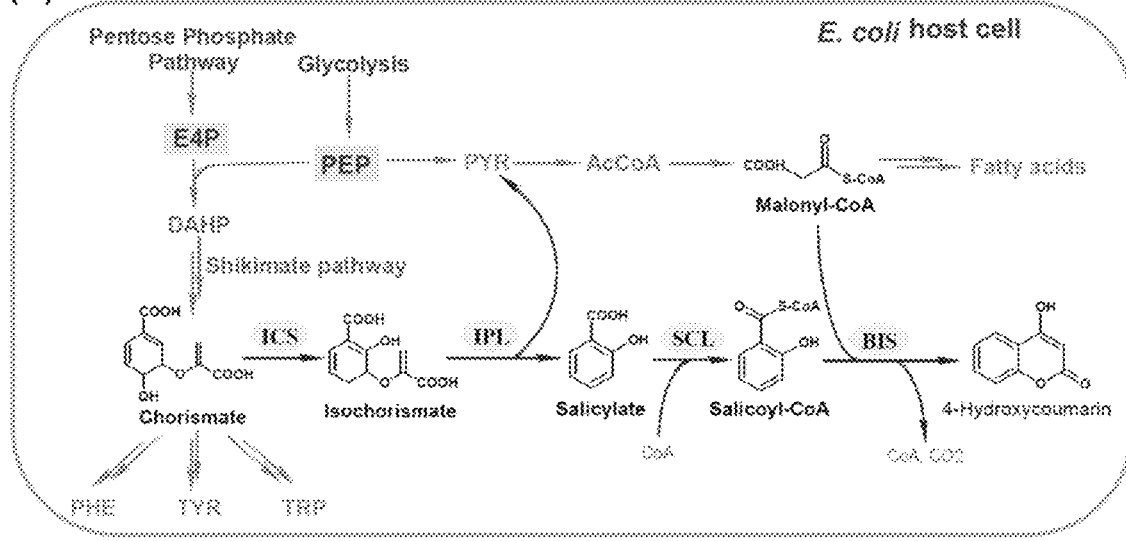

Described herein is an artificial method for the microbial biosynthesis of 4-hydroxycoumarin (4HC), and genetically engineered microbes for producing 4HC. The pathway scheme is shown in FIG. 2B. Chorismate, an intermediate of the shikimate pathway, can be used as a substrate by an isochorismate synthase to produce isochorismate. The isochorismate produced can be converted to salicylate and pyruvate by the action of an isochorismate pyruvate lyase. The salicylate can be converted to salicoyl-CoA by a salicylate:CoA ligase. The final step in the formation of 4-hydroxycoumarin is the condensation of a salicoyl-CoA and a malonyl-CoA catalyzed by a 4HC forming enzyme, such as a biphenyl synthase.

The microbial pathway described herein for the production of 4HC from a chorismate intermediate includes an enzyme having isochorismate synthase activity. As used herein, "isochorismate synthase" and "ICS" refer to a protein that, regardless of its common name or native function, catalyses the conversion of chorismate to isochorismate (see FIG. 2B), and a protein catalysing such a conversion has isochorismate synthase activity. Methods for determining whether a protein has isochorismate synthase activity are described in Example 1.

Enzymes having isochorismate synthase activity are known to the skilled worker and are easily obtained. A coding region encoding a protein having isochorismate synthase activity may be obtained from a suitable biological source, such as a microbial cell, using standard molecular cloning techniques. Examples of coding regions include, but are not limited to, those that encode PchA (Serino et al., *Mol. Gen. Genet.* 249, 217-228 (1995)), EntC (Liu et al., *Biochemistry (Mosc.)* 29, 1417-1425 (1990)) and MenF (Daruwala et al., *J. Bacteriol.* 179, 3133-3138 (1997)). Suitable microbes that may harbor coding regions encoding enzymes having isochorismate synthase activity include, but are not limited to, *Mycobacterium* species, *Pseudomonas* species including *P. aeruginosa, E. coli, Bacillus subtilis, Klebsiella pneumonia, Bacillus cereus, Salmonella enteric, Staphylococcus aureus, Mycobacterium tuberculosis, Acinetobacter baumannii, Listeria monocytogenes, Yersinia pestis*, as well as other genera. Coding regions may be isolated using polymerase chain reaction (PCR) with primers designed by standard primer design software which is commonly used in the art. Exemplary primers for use in isolating a coding region encoding a protein having isochorismate synthase activity are shown in Table 3. Suitable coding sequences are easily ligated into any standard expression vector by the skilled person. In one embodiment, a protein having isochorismate synthase activity is, or is structurally similar to, a reference protein that has the amino acid sequence of SEQ ID NO:1 (GenBank number NP_415125.1).

The microbial pathway described herein for the production of 4HC from a chorismate intermediate includes an enzyme having isochorismate pyruvate lyase activity. As used herein, "isochorismate pyruvate lyase" and "IPL" refer to a protein that, regardless of its common name or native function, catalyses the conversion of isochorismate to salicylate and pyruvate (see FIG. 2B), and a protein catalysing such a conversion has isochorismate pyruvate lyase activity. Methods for determining whether a protein has isochorismate pyruvate lyase activity are described in Example 1.

Enzymes having isochorismate pyruvate lyase activity are known to the skilled worker and are easily obtained. A coding region encoding a protein having isochorismate pyruvate lyase activity may be obtained from a suitable biological source, such as a microbial cell, using standard molecular cloning techniques. Examples of coding regions include, but are not limited to, those that encode PchB from *P. aeruginosa* (PaPchB, Serino et al., *Mol. Gen. Genet.* 249, 217-228 (1995)) and *P. fluorescence* (PfPchB). Suitable microbes that may harbor coding regions encoding enzymes having isochorismate pyruvate lyase activity include, but are not limited to, *Mycobacterium* species, other *Pseudomonas* species, *Burkholderia pseudomallei, Mycobacterium tuberculosis, Vibrio nigripulchritudo, Burkholderia cenocepacia, Vibrio nigripulchritudo, Serratia plymuthica, Acidithiobacillus ferrooxidans, Serratia fonticola*, as well as other genera. Coding regions may be isolated using polymerase chain reaction (PCR) with primers designed by standard primer design software which is commonly used in the art. Exemplary primers for use in isolating a coding region encoding a protein having isochorismate pyruvate lyase activity are shown in Table 3. Suitable coding sequences are easily ligated into any standard expression vector by the skilled person. In one embodiment, a protein having isochorismate pyruvate lyase activity is, or is structurally similar to, a reference protein that has the amino acid sequence of SEQ ID NO:2 (GenBank number NP_252920.1).

The microbial pathway described herein for the production of 4HC from a chorismate intermediate includes an enzyme having salicylate:CoA ligase activity. As used herein, "salicylate:CoA ligase" and "SCL" refer to a protein that, regardless of its common name or native function, catalyses the conversion of salicylate to salicoyl-CoA (see FIG. 2B), and a protein catalysing such a conversion has salicylate:CoA ligase activity. Methods for determining whether a protein has salicylate:CoA ligase activity are described in Example 1.

Enzymes having salicylate:CoA ligase activity are known to the skilled worker and are easily obtained. A coding region encoding a protein having salicylate:CoA ligase activity may be obtained from a suitable biological source, such as a microbial cell, using standard molecular cloning techniques. Examples of coding regions include, but are not limited to, those that encode SdgA (involved in salicylate degradation in *Streptomyces* sp. WA46, Ishiyama et al., 2004, Appl. Environ. Microbiol. 70:1297-1306), MdpB2 (involved in maduropeptin biosynthesis in *Actinomadura madurae* ATCC39144, Ling, et al., 2010, J. Am. Chem. Soc. 132:12534-12536), and SsfL1 (involved in tetracycline SF2575 biosynthesis in *Streptomyces* sp. SF2575, Pickens et al., 2009, J. Am. Chem. Soc. 131:17677-17689). Other examples of enzymes having salicylate:CoA ligase activity include some benzoate:CoA ligases (Geissler et al., 1988, *J. Bacteriol.* 170:1709-1714, and Beuerle et al., 2002, Arch. Biochem. Biophys. 400:258-264). Suitable microbes that may harbor coding regions encoding enzymes having salicylate:CoA ligase activity include, but are not limited to, *Streptomyces* sp., *Actinomadura* sp., *Rhodopseudomonas* sp., *Magnetospirillum* sp., *Clarkia breweri, Thauera aromatics, Geobacter metallireducens*, as well as other genera. Coding regions may be isolated using polymerase chain reaction (PCR) with primers designed by standard primer design software which is commonly used in the art. Exemplary primers for use in isolating a coding region encoding a protein having salicylate:CoA ligase activity are shown in Table 3. Suitable coding sequences are easily ligated into any standard expression vector by the skilled person. In one embodiment, a protein having salicylate:CoA ligase activity is, or is structurally similar to, a reference protein that has the amino acid sequence of SEQ ID NO:3 (GenBank number BAC78380.1).

The microbial pathway described herein for the production of 4HC from a chorismate intermediate includes an enzyme having 4HC-forming activity. As used herein, "4HC-forming" and "BIS" refer to a protein that, regardless of its common name or native function, catalyses the condensation of a salicoyl-CoA and a malonyl-CoA to form 4HC (see FIG. 2B), and a protein catalysing such a conversion has 4HC-forming activity. Methods for determining whether a protein has 4HC-forming activity are described in Example 1.

Enzymes having 4HC-forming activity are known to the skilled worker and are easily obtained. A coding region encoding a protein having 4HC-forming activity may be obtained from a suitable biological source, such as a microbial cell, using standard molecular cloning techniques. Examples of coding regions include, but are not limited to, those encoding biphenyl synthases, such as BIS3 from *Sorbus aucuparia* (Liu et al., *Plant Mol. Biol.* 72, 17-25 (2010)), and a FabH-like quinolone synthase (β-ketoacyl-ACP synthase III (FabH)-type quinolone synthase) PqsD from *P. aeruginosa* (Zhang et al., *J. Biol. Chem.* 283, 28788-28794 (2008)). Suitable microbes that may harbor coding regions encoding enzymes having 4HC-forming activity include, but are not limited to, *Sorbus aucupari* and *P. aeruginosa*, as well as other genera. Coding regions may be isolated using polymerase chain reaction (PCR) with primers designed by standard primer design software which is commonly used in the art. Exemplary primers for use in isolating a coding region encoding a protein having 4HC-forming activity are shown in Table 3. Suitable coding sequences are easily ligated into any standard expression vector by the skilled person. In one embodiment, a protein having 4HC-forming activity is, or is structurally similar to, a reference protein that has the amino acid sequence of SEQ ID NO:4 (GenBank number NP_249690.1).

Other examples of proteins useful in the methods described herein include those that are structurally similar to the amino acid sequence of SEQ ID NO:1, SEQ ID NO:2, SEQ ID NO:3, or SEQ ID NO:4. An isochorismate synthase that is structurally similar to the amino acid sequence of SEQ ID NO:1 has isochorismate synthase activity. An isochorismate pyruvate lyase that is structurally similar to the amino acid sequence of SEQ ID NO: 2 has isochorismate pyruvate lyase activity. A salicylate:CoA ligase that is structurally similar to the amino acid sequence of SEQ ID NO:3 has salicylate:CoA ligase activity. A 4HC-forming enzyme that is structurally similar to the amino acid sequence of SEQ ID NO:4 has 4HC-forming activity.

Structural similarity of two proteins can be determined by aligning the residues of the two proteins (for example, a candidate protein and any appropriate reference protein described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference protein may be a protein described herein. A candidate protein is the protein being compared to the reference protein. A candidate protein may be isolated, for example, from a microbe, or can be produced using recombinant techniques, or chemically or enzymatically synthesized.

Unless modified as otherwise described herein, a pair-wise comparison analysis of amino acid sequences can be carried out using the Blastp program of the BLAST 2 search algorithm, as described by Tatiana et al., (*FEMS Microbiol Lett*, 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, word-size=3, and filter on. Alternatively, polypeptides may be compared using the BESTFIT algorithm in the GCG package (version 10.2, Madison Wis.).

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a protein described herein may be selected from other members of the class to which the amino acid belongs. For example, it is known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, non-polar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2.

Thus, as used herein, a candidate protein useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to a reference amino acid sequence.

Alternatively, as used herein, a candidate protein useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

Optionally, the microbe may be further genetically engineered to increase the amount of chorismate and/or malonyl-CoA compared to a control cell. Rate limiting steps in the production of chorismate and malonyl-CoA are known and can be manipulated to result in more of those intermediates. Regarding chorismate production, the 3-deoxy-D-arabino-heptulosonate-7-phosphate synthases encoded by aroG, aroF, and aroH in *E. coli* are feedback-inhibited by phenylalanine, tyrosine, and tryptophan, respectively (Kikuchi et al. *Appl. Environ. Microbiol.* 63, 761-762 (1997). Feedback inhibition resistant (fbr) variants of these enzymes can be engineered, for example, by introducing point mutations. For instance, a feedback inhibition resistant variant aroG$^{fbr}$ can be generated by introducing a point mutation that results in an Asp-146-Asn mutation in the enzyme. Erythrose-4-phosphate (E4P) is a rate limiting intermediate in the shikimate pathway for the production of chorismate, and the availability of E4P can be alleviated by over-expressing transketolase (encoded by tktA). Phosphoenolpyruvate (PEP) is also a rate limiting intermediate in the shikimate pathway for the production of chorismate, and the availability of PEP can be alleviated by over-expressing PEP synthase (encoded by ppsA), (Lutke-Eversloh et al. *Appl. Microbiol. Biotechnol.* 75, 103-110 (2007)). Shikimate kinase (encoded by aroK/aroL) is another bottleneck which can be eliminated by the over-expression of aroL (Luetke-Eversloh et al. *Metab. Eng.* 10, 69-77 (2008)). The coding regions encoding these enzymes may be isolated using polymerase chain reaction (PCR) with primers designed by standard primer design software which is commonly used in the art. Exemplary primers for use in isolating such coding regions are shown in Table 3. Thus, an engineered cell described herein may optionally include a mutation conferring feedback inhibition resistance in one or more of the 3-deoxy-D-arabino-heptulosonate-7-phosphate synthases encoded by aroG, aroF, and aroH, such as aroG$^{fbr}$, increased expression of a PEP synthase encoded by ppsA, increased expression of a transketolase encoded by tktA, increased expression of a shikimate kinase encoded by aroK/aroL, or a combination thereof. In one embodiment, the engineered cell includes aroL, ppsA, tktA, and aroG$^{fbr}$.

A protein useful in the methods described herein may include other amino acid residues. In one embodiment, the additional amino acids are heterologous amino acids. As used herein, "heterologous amino acids" refers to amino acids that are not normally or naturally found flanking the amino acid sequence of an ICS, IPL, SCL, or BIS protein in a microbial cell. A protein that includes heterologous amino acids may be referred to as a fusion polypeptide.

In one embodiment, the additional amino acid sequence may be useful for purification of the fusion polypeptide by affinity chromatography. Various methods are available for the addition of such affinity purification moieties to proteins. Representative examples include, for instance, polyhistidine-tag (His-tag) and maltose-binding protein (see, for instance, Hopp et al. (U.S. Pat. No. 4,703,004), Hopp et al. (U.S. Pat. No. 4,782,137), Sgarlato (U.S. Pat. No. 5,935,824), and Sharma (U.S. Pat. No. 5,594,115)). In one embodiment, the additional amino acid sequence may be a carrier polypeptide. The carrier polypeptide may be used to increase the immunogenicity of the fusion polypeptide to increase production of antibodies that specifically bind to a protein described herein. In another embodiment, the additional amino acid sequence may be a fluorescent polypeptide (e.g., green, yellow, blue, or red fluorescent proteins) or other amino acid sequences that can be detected in a cell or in vitro. If a protein described herein includes an additional amino acid sequence not normally or naturally associated with the polypeptide, the additional amino acids are not considered when percent structural similarity to a reference amino acid sequence is determined.

Proteins described herein can be produced using recombinant DNA techniques, such as an expression vector present in a cell. Such methods are routine and known in the art. The proteins may also be synthesized in vitro, e.g., by solid phase peptide synthetic methods. The solid phase peptide synthetic methods are routine and known in the art. A protein produced using recombinant techniques or by solid phase peptide synthetic methods can be further purified by routine methods, such as fractionation on immunoaffinity or ion-exchange columns, ethanol precipitation, reverse phase HPLC, chromatography on silica or on an anion-exchange resin such as DEAE, chromatofocusing, SDS-PAGE, ammonium sulfate precipitation, gel filtration using, for example, Sephadex G-75, or ligand affinity.

Also provided are polynucleotides encoding an ICS, IPL, SCL, or BIS protein. Given the amino acid sequence of an ICS, IPL, SCL, or BIS protein described herein, a person of ordinary skill in the art can determine the full scope of polynucleotides that encode that amino acid sequence using conventional, routine methods. The class of nucleotide sequences encoding a selected protein sequence is large but finite, and the nucleotide sequence of each member of the class may be readily determined by one skilled in the art by reference to the standard genetic code, wherein different nucleotide triplets (codons) are known to encode the same amino acid.

An ICS, IPL, SCL, and/or a BIS polynucleotide described herein may include heterologous nucleotides flanking the coding region encoding the protein. The boundaries of a coding region are generally determined by a translation start codon at its 5' end and a translation stop codon at its 3' end. As used herein, "heterologous nucleotides" refers to a nucleotide sequence that is not normally or naturally found flanking an open reading frame in a cell encoding an ICS, IPL, SCL, or BIS protein. Examples of heterologous nucleotides include, but are not limited to, a regulatory sequence. The number of heterologous nucleotides may be, for instance, at least 10, at least 100, or at least 1000.

A polynucleotide described herein, such as an ICS, IPL, SCL, or BIS protein, can be present in a vector. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard ligation techniques known in the art. See, e.g., Sambrook et al, *Molecular Cloning: A Laboratory Manual.*, Cold Spring Harbor Laboratory Press (1989). A vector can provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, and transposon vectors. A vector may be replication-proficient or replication-deficient. A vector may result in integration into a cell's genomic DNA. Typically, a vector is capable of replication in a host cell, such as *E. coli*.

Selection of a vector depends upon a variety of desired characteristics in the resulting construct, such as a selection marker, vector replication rate, and the like. Suitable host cells for cloning or expressing the vectors herein are prokaryotic or eukaryotic cells. Suitable eukaryotic cells include mammalian cells, such as yeast cells, murine cells, and human cells. Suitable prokaryotic cells include eubacteria, such as gram-negative organisms, for example, *E. coli*.

An expression vector optionally includes regulatory sequences operably linked to a polynucleotide encoding a protein, such as an ICS, IPL, SCL, or BIS protein. An example of a regulatory sequence is a promoter. A promoter may be functional in a host cell used, for instance, in the construction and/or characterization of a polynucleotide encoding a protein described herein, and/or may be functional in the ultimate recipient of the vector. A promoter may be inducible, repressible, or constitutive, and examples of each type are known in the art. A polynucleotide encoding a protein described herein may also include a transcription terminator. Suitable transcription terminators are known in the art.

The four coding regions (ICS, IPL, SCL, and BIS) may be on separate plasmids, all four coding regions may be on one plasmid, or different coding regions may be grouped together in some combination thereof. Likewise, the four coding regions may be integrated into a cell's genomic DNA at four different locations, at one location, or different coding regions may be grouped together in some combination thereof. For instance, a plasmid may include one coding region and a second plasmid may include the other three coding regions, or in another embodiment one plasmid may include two of the coding regions and a second plasmid may include the other two coding regions. In one embodiment, one plasmid includes a coding region encoding an ICS and another coding region encoding an IPL, while a second plasmid includes a coding region encoding a SCL and another coding region encoding a BIS. The plasmid may be high copy number (copies in a cell in the 100's) or low copy number (2-5 copies in a cell). In one embodiment, two or more coding regions may be expressed as an operon, e.g., a single promoter drives expression of more than one coding region.

Polynucleotides described herein can be produced in vitro or in vivo. For instance, methods for in vitro synthesis include, but are not limited to, chemical synthesis with a conventional DNA/RNA synthesizer. Commercial suppliers of synthetic polynucleotides and reagents for in vitro synthesis are known. Methods for in vitro synthesis also include, for instance, in vitro transcription using a circular or linear expression vector in a cell free system. Expression vectors can also be used to produce a polynucleotide in a cell, and the polynucleotide may then be isolated from the cell.

The coding regions encoding proteins for production of 4HC may be introduced into a microbial cell using genetic engineering techniques. The term "microbe" is used interchangeably with the term "microorganism" and means any microscopic organism existing as a single cell, cell clusters, or multicellular relatively complex organisms. While certain embodiments are described using *E. coli*, the microbes and methods of use are not limited to *E. coli* and there are a number of other options for microbes suitable for engineering to synthesize 4HC and for use in the methods described herein. The suitable microbial hosts for the synthesis of 4HC as described herein include, but are not limited to, a wide variety of bacteria, archaea, and yeast including members of the genera *Escherichia* (such as *E. coli*), *Pseudomonas* spp. (such as *P. putida*), *Thermus thermophilus*, *Salmonella*, *Clostridium*, *Zymomonas*, *Bacillus* (such as *B. subtilis* and *B. licheniformis*), *Rhodococcus* (such as *R. erythropolis*), *Alcaligenes* (such as *A. eutrophus*), *Klebsiella*, *Paenibacillus* (such as *P. macerans*), *Lactobacillus* (such as *L. plantarum*), *Enterococcus* (such as *E. gallinarium*, *E. faecalis*, and *E. faecium*), *Arthrobacter*, *Brevibacterium*, *Corynebacterium* *Candida*, *Hansenula*, *Pichia*, cyanobacteria, and *Saccharomyces* (such as *S. cerevisiae*). Other suitable microbial hosts include algae, protozoa, microscopic plants such as green algae, and microscopic animals such as rotifers and planarians. If necessary, a coding region encoding an enzyme described herein can be modified using routine methods to reflect the codon usage bias of a microbial host cell to optimize expression of a polypeptide.

A cell that has been genetically engineered to produce 4HC from a chorismate intermediate may be referred to as a "host" cell, a "recombinant" cell, a "metabolically engineered" cell, a "genetically engineered" cell or simply an "engineered" cell. These and similar terms are used interchangeably. A genetically engineered cell refers to a microbe that has been altered by the hand of man by the introduction of at least one exogenous polynucleotide. Thus, in one embodiment, a genetically engineered cell contains one or more exogenous polynucleotides which have been created through standard molecular cloning techniques to bring together genetic material that is not natively found together. For example, a microbe is a genetically engineered microbe by virtue of introduction of an exogenous polynucleotide. "Engineered" also includes a microbe that has been genetically manipulated such that one or more endogenous nucleotides have been altered. For example, a microbe is an engineered microbe by virtue of introduction of an alteration of endogenous nucleotides into a suitable microbe. For instance, a regulatory region, such as a promoter, could be altered to result in increased or decreased expression of an operably linked endogenous coding region. DNA sequences used in the construction of recombinant DNA molecules can originate from any species. For example, bacterial DNA may be joined with fungal DNA. Alternatively, DNA sequences that do not occur anywhere in nature may be created by the chemical synthesis of DNA, and incorporated into recombinant molecules. Proteins that result from the expression of recombinant DNA are often termed recombinant proteins. Examples of recombination may include inserting foreign polynucleotides into a cell, inserting synthetic polynucleotides into a cell, or relocating or rearranging polynucleotides within a cell. Any form of recombination may be considered to be genetic engineering and therefore any recombinant cell may also be considered to be a genetically engineered cell.

Genetically engineered cells are also referred to as "metabolically engineered" cells when the genetic engineering modifies or alters one or more particular metabolic pathways so as to cause a change in metabolism. The goal of metabolic engineering is to improve the rate and conversion of a substrate into a desired product. General laboratory methods for introducing and expressing or overexpressing native and normative proteins such as enzymes in many different cell types (including bacteria, archaea, and yeasts,) are routine and known in the art; see, e.g., Sambrook et al, *Molecular Cloning: A Laboratory Manual.*, Cold Spring Harbor Laboratory Press (1989), and *Methods for General and Molecular Bacteriology*, (eds. Gerhardt et al.) American Society for Microbiology, chapters 13-14 and 16-18 (1994).

The introduction of coding regions encoding the enzymes of the metabolic pathway for the production of 4HC from a chorismate intermediate into a cell involves expression or overexpression of the enzymes. An enzyme is "overexpressed" in a recombinant cell when the enzyme is expressed at a level higher than the level at which it is expressed in a comparable wild-type cell. In cells that do not express a particular endogenous enzyme, or in cells in which the enzyme is not endogenous (i.e., the enzyme is not native to the cell), any level of expression of that enzyme in the cell is deemed an "overexpression" of that enzyme for purposes of the present invention.

As will be appreciated by a person of skill in the art, overexpression of an enzyme can be achieved through a number of molecular biology techniques. For example, overexpression can be achieved by introducing into the host cell one or more copies of a polynucleotide encoding the desired enzyme. The polynucleotide encoding the desired enzyme may be endogenous or exogenous to the host cell. Typically, the polynucleotide is introduced into the cell using a vector. The polynucleotide may be circular or linear, single-stranded or double stranded, and can be DNA, RNA, or any modification or combination thereof. The vector can be any molecule that may be used as a vehicle to transfer genetic material into a cell. Examples of molecular biology techniques used to transfer nucleotide sequences into a microorganism include, without limitation, transfection, electroporation, transduction, and transformation. These methods are routine and known in the art. Insertion of a vector into a target cell is usually called transformation for bacterial cells and transfection for eukaryotic cells, however insertion of a viral vector is often called transduction. The terms transformation, transfection, and transduction, for the purpose of the present invention, are used interchangeably herein.

Also provided herein are methods for producing 4HC using the engineered cells described herein. Briefly, and as described and illustrated in more detail elsewhere herein, the host cell is engineered to contain a novel biosynthetic pathway. Specifically, the host cell is engineered to overexpress an enzyme having isochorismate synthase activity, isochorismate pyruvate lyase activity, salicylate:CoA ligase activity, 4HC-forming activity, or a combination thereof. In one embodiment, the method includes culturing the engineered microbe under conditions suitable for the production of 4-hydroxycoumarin. The cell may be one expressing an endogenous isochorismate synthase, an endogenous isochorismate pyruvate lyase, an endogenous salicylate:CoA ligase, a 4HC-forming protein, or a combination thereof. Alternatively, the cell may be a recombinant cell that has been engineered to express isochorismate synthase, isochorismate pyruvate lyase, salicylate:CoA ligase, and/or 4HC-forming protein at a level greater than a control cell. In one embodiment, the amount of 4HC produced by an engineered cell described herein after 24 hours incubation in a shake flask kept under constant agitation is at least 0.1 gram/liter (g/L), at least 0.25 g/L, at least 0.5 g/L, or at least 0.75 g/L. In one embodiment, the amount of 4HC produced by an engineered cell described herein after 24 hours incubation in a shake flask kept under constant agitation is no greater than 2 g/L, no greater than 1.75 g/L, no greater than 1.5 g/L, or no greater than 1.25 g/L.

In one embodiment, the method includes incubating isolated isochorismate synthase, isochorismate pyruvate lyase, salicylate:CoA ligase, and 4HC-forming proteins with chorismate under conditions suitable to produce 4HC. The cell used as a source of the proteins may be a recombinant cell that expresses one or more of the proteins at a level greater than a control cell. Alternatively, one or more of the proteins may be produced chemically or synthetically.

The 4HC produced via the novel biosynthetic pathway can be isolated and optionally purified from any genetically engineered cell described herein. It can be isolated directly from the cells, or from the culture medium, for example, during an aerobic or anaerobic fermentation process. Isolation and/or purification can be accomplished using known and routine methods. The 4HC may be used in any application, including as the starting point for the synthesis of other compounds.

The methods described herein also include using the 4-hydroxycoumarin produced by the microbe as the starting point for the synthesis of other compounds. Accordingly, provided herein are methods for producing compounds that include a 4-hydroxycoumarin structure. In one embodiment, a compound that includes a 4-hydroxycoumarin structure is an anticoagulant. Examples of other compounds that include the 4-hydroxycoumarin structure include, for instance, wayfarin, dicoumarol, and synthtic 4-hydroxycoumarins such as phenprocoumon and acenocoumarol. Wayfarin may be produced by, for instance, adding the precursor benzyldeneacetone and the catalyst (S,S)-1,2-diphenylethylenediamine to the 4-hydroxycoumarin produced by a microbe as described herein. The 4-hydroxycoumarin may be present in the culture with the microbes, or may be enriched or isolated.

The genetically engineered cells described herein can be cultured aerobically or anaerobically, or in a multiple phase fermentation that makes use of periods of anaerobic and aerobic fermentation. The decision on whether to use anaerobic and aerobic fermentation depends on variables familiar to the skilled person. Fed-batch fermentation, batch fermentation, continuous fermentation, or any other fermentation method may be used.

In various embodiments different supplements may be included in the medium in which the engineered cells are grown. In one embodiment, the medium may be supplemented with yeast extract from 1 to 20 grams per liter to improve cell growth and 4HC production. The method may also include supplying at least one carbon source such as glucose, xylose, sucrose, arabinose, glycerol, and/or galactose.

Importantly, the present invention permits a "total synthesis" or "de novo" biosynthesis of 4HC in the genetically engineered cell. In other words, it is not necessary to supply the genetically engineered cells with precursors or intermediates; 4HC can be produced using ordinary inexpensive carbon sources such as glucose and the like.

The present invention is illustrated by the following examples. It is to be understood that the particular examples, materials, amounts, and procedures are to be interpreted broadly in accordance with the scope and spirit of the invention as set forth herein.

Example 1

4-Hydroxycoumarin (4HC) type anticoagulants (e.g. warfarin) are known to play a significant role in the treatment of thromboembolic diseases—a leading cause of patient morbidity and mortality worldwide. 4HC serves as an immediate precursor of these synthetic anticoagulants. Although 4HC was initially identified as a naturally occurring product, its biosynthesis has not been fully elucidated. Here we present the design, validation, in vitro diagnosis, and optimization of an artificial biosynthetic mechanism leading to the microbial biosynthesis of 4HC. Remarkably, function-based enzyme bioprospecting leads to the identification of a characteristic FabH-like quinolone synthase from *Pseudomonas aeruginosa* with high efficiency on the 4HC-forming reaction, which promotes the high-level de novo biosynthesis of 4HC in *Escherichia coli* (~500 mg/L in shake flasks) and further in situ semi-synthesis of warfarin. This work holds scale-up potential for microbial production of 4HC and opens up the possibility of biosynthesizing diverse coumarin molecules with pharmaceutical importance.

Materials and Methods

Strains, Plasmids, and Media.

*E. coli* strain XL1-Blue was used for plasmid propagation and gene cloning; BL21 Star™ (DE3) was used for recombinant protein expression and purification; BW25113 containing F' from XL1-Blue was used as the host strain for the biosynthesis of salicylate and 4HC. The characteristics of all the strains and plasmids used in this study were described in Table 1. Luria-Bertani (LB) medium was used to grow *E. coli* cells for plasmid construction, propagation, and inoculum preparation. The biosynthesis medium M9Y contains (per liter): glycerol (20 g), yeast extract (5 g), $NH_4Cl$ (1 g), $Na_2HPO_4$ (6 g), $KH_2PO_4$ (3 g), NaCl (0.5 g), $MgSO_4 \cdot 7H_2O$ (2 mmol), $CaCl_2 \cdot 2H_2O$ (0.1 mmol), vitamin B1 (1.0 mg). 100 µg/ml of ampicillin, 50 µg/ml of kanamycin and/or 30 µg/ml of chloramphenicol were added when necessary.

TABLE 1

Strains and plasmids used in this study

| Plasmid and Strain | Characteristics | Source |
|---|---|---|
| Plasmid | | |
| pZE12-luc | ColE1 ori; $Amp^r$; $P_L$lacO-1; luc | Ref. 1 |
| pCS27 | p15A ori; $Kan^r$; $P_L$lacO-1; MCS* | Ref. 1 |
| pSA74 | pSC101* ori; $Cm^r$; $P_L$lacO-1; MCS | Ref. 2 |
| pETDUET-1 | pBR322 ori; $Amp^r$ two T7 promoters; two MCS | Novagen |
| pZE-BIS3-SdgA | From pZE12-luc, $P_L$lacO-1; bis3-sdgA | This study |
| pZE-PS | From pZE12-luc, $P_L$lacO-1; pqsD-sdgA | This study |
| pZE-EP | From pZE12-luc, $P_L$lacO-1; entC-pfpchB | This study |
| pZE-EP-PS | From pZE12-luc, dual operons entC-pfpchB and pqsD-sdgA, both with $P_L$lacO-1 | This study |
| pCS-PS | From pCS27, $P_L$lacO-1; pqsD-sdgA | This study |
| pZE-EPBS | From pZE12-luc, $P_L$lacO-1; entC-pfpchB-bis3-sdgA | This study |
| pZE-EPPS | From pZE12-luc, $P_L$lacO-1; entC-pfpchB-pqsD-sdgA | This study |
| pCS-APTA | From pCS27, $P_L$lacO-1; aroL-ppsA-tktA-aroG$^{fbr}$ | This study |

TABLE 1-continued

Strains and plasmids used in this study

| Plasmid and Strain | Characteristics | Source |
|---|---|---|
| pZE-EP-APTA | From pZE12-luc, dual operons entC-pfpchB and aroL-ppsA-tktA-aroG$^{fbr}$, both with P$_L$lacO-1 | This study |
| pSA-ACCB | From pSA74, P$_L$lacO-1; accA-accD-accB-accC-birA | This study |

Strain

| E. coli XL1-Blue | recA1 endA1 gyrA96 thi-1 hsdR17 supE44 relA1 lac [F' proAB lacI$^q$Z ΔM15 Tn10 (Tet$^R$)] | Stratagene |
| E. coli BW25113 | Δ(araD-araB), ΔlacZ (::rrnB-3), λ-, rph-1, Δ(rhaD-rhaB), hsdR | Yale CGSC |
| Strain A | BW25113/F' harboring pZE-EP-PS | This study |
| Strain B | BW25113/F' harboring pZE-EP and pCS-PS | This study |
| Strain C | BW25113/F' harboring pZE-EPPS | This study |
| Strain D | BW25113/F' harboring pZE-EP-APTA and pCS-PS | This study |
| Strain E | BW25113/F' harboring pZE-EPPS and pCS-APTA | This study |

*MCS: multiple cloning sites.
Reference 1, Lin and Yan, *Microb. Cell. Fact.* 11, 42 (2012);
Reference 2, Huo et al., *Nat. Biotechnol.* 29, 346-351 (2011).

DNA Manipulation.

The plasmids were generated via either regular cloning or Gibson assembly (Gibson et al. *Nat. Methods* 6, 343-345 (2009)). The plasmid pETDUET-1 was used for the overexpression and purification of recombinant proteins with an N-terminal His tag; while pZE12-luc, pCS27, and pSA74 are compatible plasmids used for expressing multiple enzymes involved in the biosynthetic mechanism. The codon-optimized BIS3 cDNA was synthesized by Eurofins MWG Operon. The cDNAs of SdgA and MdpB2 obtained from Dr. Julian Davies and Dr. Ben Shen, respectively. Genes of EntC and MenF were cloned from the genomic DNA of E. coli MG1655. The coding sequences of PqsD, PchA, and PaPchB were cloned from the *P. aeruginosa* PAO1 genomic DNA. The PfPchB gene was cloned from the *P. fluorescence* Pf5 genomic DNA. To purify the proteins, the genes of SdgA, MdpB2, EntC, MenF, PchA, PaPchB, PfPchB, and BIS3 were separately sub-cloned into pETDUET-1. All the genes were fused in frame with the his-tag DNA sequence using BamHI and PstI, except for PchA (using BamHI and SalI) and MdpB2 (using BamHI and HindIII). To construct pZE-BIS3-SdgA, the genes of BIS3 and SdgA were digested with KpnI/NdeI and NdeI/XbaI, respectively, and then ligated with the KpnI/XbaI digested pZE12-luc fragment via simultaneous three-piece ligation. To construct pZE-PS, the BIS3 gene was replaced with the PqsD cDNA using the same restriction sites. For pCS-PS, the same strategy was employed but using pCS27 as the backbone and different restriction enzymes Acc65I, NdeI, and BamHI. To construct pZE-EP, the genes of EntC and PfPchB were digested with KpnI/NdeI and NdeI/SphI, respectively, and then ligated with the KpnI/SphI digested pZE12-luc fragment via three-piece ligation. The plasmid pZE-EP-PS harboring two operons, P$_L$lacO1-EntC-PfPchB and P$_L$lacO1-PqsD-SdgA, was assembled as described by Gilson using the plasmids pZE-EP and pZE-PS as templates and pZE12-luc as the backbone (Gibson et al. *Nat. Methods* 6, 343-345 (2009)). pZE-EPBS and pZE-EPPS were generated by inserting the BIS3/PqsD and SdgA genes into pZE-EP using the restriction sites SphI, NdeI, and XbaI via three-piece ligation. pCS-APTA was constructed by inserting aroL, ppsA, tktA, and aroG$^{fbr}$ through two rounds of three-piece ligation using KpnI/NdeI/SalI and XhoI/SphI/HindIII. The similar strategy was used to construct pSA-ACCB using Acc65I/PstI/SalI and SalI/EcoRI/BamHI. The plasmid pZE-EP-APTA was constructed by inserting the P$_L$lacO1-APTA operon from pCS-APTA into pZE-EP using SaCI and SpeI.

Information of the pathway enzymes used in this study is summarized in Table 2. The primers used are listed in Table 3.

TABLE 2

Information of the pathway enzymes investigated as described herein.

| Enzyme | Activity | Information |
|---|---|---|
| SdgA | Salicylate:CoA ligase | From *Streptomyces* sp. Strain WA46. Previously reported by Ishiyama et al (Ref 1). |
| MdpB2 | | We determined its kinetic parameters in this study for the first time. From *Actinomadura madurae* ATCC39144. Previously characterized by Ling et al (Ref 2). |
| EntC | Isochorismate synthase | From *E. coli* MG1655. Previously characterized by Liu et al (Ref 3). |
| MenF | | From *E. coli* MG1655. Previously characterized by Daruwala et al (Ref 4). |
| PchA | | From *Pseudomonas aeruginosa* PAO1. Previously characterized by Serino et al (Ref 5). |
| PaPchB | Isochorismate pyruvate lyase | From *Pseudomonas aeruginosa* PAO1. Previously characterized by Serino et al (Ref 5). |
| PfPchB | | From *Pseudomonas fluorescence* Pf-5. A putative IPL was not characterized before, sharing 62% identity with PaPchB. |
| BIS3 | 4HC-forming enzyme | Previously characterized as a biphenyl synthase from *Sorbus aucuparia*, also has the activity to form 4HC (Ref 6). |
| PqsD | | From *Pseudomonas aeruginosa* PAO1. Previously identified as a quinolone synthase (Ref 7). We identified its 4HC-forming activity in vivo for the first time. |

Reference 1, Ishiyama et al. *Appl. Environ. Microbiol.* 70, 1297-1306 (2004);
Reference 2, Ling et al. *J. Am. Chem. Soc.* 132, 12534-12536 (2010);
Reference 3, Liu et al., *Biochemistry (Mosc.)* 29, 1417-1425 (1990);
Reference 4, Daruwala et al., *J. Bacteriol.* 179, 3133-3138 (1997);
Reference 5, Serino et al., *Mol. Gen. Genet.* 249, 217-228 (1995);
Reference 6, Liu et al., *Plant Mol. Biol.* 72, 17-25 (2010);
Reference 7, Zhang et al., *J. Biol. Chem.* 283, 28788-28794 (2008).

TABLE 3

Primers used as described herein.

| Primer | Sequence (SEQ ID NO) | Use |
|---|---|---|
| yy123(BamHI) | gggaaaggatccggatacgtcactggctgaggaagtac (5) | To clone EntC gene into |
| yy124(PstI) | gggaaactgcagttaatgcaatccaaaaacgttcaacatggtag (6) | pETDUET-1 |
| yy125(BamHI) | gggaaaggatccgcaatcacttactacggcgctgg (7) | To clone MenF gene into |
| yy126(PstI) | gggaaactgcagctattccatttgtaataaagtacgcagccc (8) | pETDUET-1 |
| yy127(BamHI) | gggaaaggatccgagccggctggcgcccctgagccagt (9) | To clone PchA gene into |
| yy128(SalI) | gggaaagtcgactcaggcgacgccgcgctgcaa (10) | pETDUET-1 |
| yy131(BamHI) | gggaaaggatccgaaaactcccgaagactgcacc (11) | To clone PaPchB gene into |
| yy132(PstI) | gggaaactgcagtcatgcggcaccccgtgtct (12) | pETDUET-1 |
| yy133(BamHI) | gggaaaggatccgctggccttcgaccccatgaatt (13) | To clone PfPchB gene into |
| yy134(PstI) | gggaaactgcagtcactcatcttgggctccttgatc (14) | pETDUET-1 |
| yy135(BamHI) | gggaaaggatccgacgcgtgagggattcgtgccct (15) | To clone SdgA gene into |
| yy136(PstI) | gggaaactgcagtcacaccgcctcgacggagtct (16) | pETDUET-1 |
| yy139(BamHI) | gggaaaggatccgaccagcattccgcgcatgatcc (17) | To clone MdpB2 gene into |
| yy140(HindIII) | gggaaaaagctttcagcgggtcgggcggtgacgaggt (18) | pETDUET-1 |
| yy141(BamHI) | gggaaaggatccggcccctgtggtcaagaacgagcct (19) | To amplifyBIS3 gene into |
| yy142(PstI) | gggaaactgcagtcagtaggtgatgaactcgctacg (20) | pETDUET-1 |
| yy215(KpnI) | gggaaaggtaccatggcccctgtggtcaagaacg (21) | To amplify BIS3 gene for |
| yy185(NdeI) | gggaaacatatgtcagtaggtgatgaactcgctacgcag (22) | pZE-BIS3-SdgA |
| yy186(NdeI) | gggaaacatatgaggagatataccatgacgcgtgagggattcgtgc (23) | To amplify SdgA gene for |
| yy187(XbaI) | gggaaatctagatcacaccgcctcgacggagtc (24) | pZE-BIS3-SdgA and pZE-PS |
| yy180(KpnI) | gggaaaggtaccatgtacgtcactggctgaggaagtac (25) | To amplify EntC gene for |
| yy181(NdeI) | gggaaacatatgttaatgcaatccaaaaacgttcaacatggtag (26) | pZE-EP |
| yy182(NdeI) | gggaaacatatgaggagatataccatgctggccttcgaccccatg (27) | To amplify PfPchB gene |
| yy183(SphI) | gggaaagcatgctcactcatcttgggctccttgatccag (28) | for pZE-EP |
| yy184(SphI) | gggaaagcatgcaggagatataccatgcccctgtggtcaagaacg (29) | To amplifyBIS3 gene for |
| yy185(NdeI) | gggaaacatatgtcagtaggtgatgaactcgctacgcag (30) | pZE-EPBS |
| yy338(KpnI) | gggaaaggtaccatgggtaatccgatcctggccg (31) | To amplify PqsD gene for |
| yy339(NdeI) | gggaaacatatgtcaacatggccggttcacctc (32) | pZE-PS |
| yy218 | aaggcggtaatacggttatccacag (33) | Gilson DNA |
| yy219 | tgagtgagctgataccgctcgc (34) | assembly |
| yy220 | gcgagcggtatcagctcactcaaggcgtatcacgaggcccttc (35) | for constructing |
| yy221 | ctgtggataaccgtattaccgcctttagggcggcggatttgtcctac (36) | pZE-EP-PS |
| yy186(NdeI) | gggaaacatatgaggagatataccatgacgcgtgagggattcgtgc (37) | To amplify SdgA gene for |
| yy401(BamHI) | gggaaaggatcctcacaccgcctcgacggagtc (38) | pCS-PS |
| yy362(SphI) | gggaaagcatgcaggagatataccatgggtaatccgatcctggccg (39) | To amplify PqsD gene for |
| yy339(NdeI) | gggaaacatatgtcaacatggccggttcacctc (40) | pZE-EPPS |
| yy188(KpnI) | gggaaaggtaccatgacacaatctcttttttctgatcgggc (41) | To amplify aroL for pCS- |
| yy189(NdeI) | gggaaacatatgtcaacaattgatcgtctgtgccagggc (42) | APTA |
| yy143(NdeI) | gggaaacatatgaggagatataccatgtccaacaatggctcgtcac (43) | To amplify ppsA for pCS- |
| yy144(SalI) | gggaaagtcgacttatttcttcagttcagccaggcttaac (44) | APTA |
| yy145(XhoI) | gggaaactcgagaggagatataccatgcctcacgtaaagagcttgcc (45) | To amplify tktA for pCS- |
| yy146(SphI) | gggaaagcatgcttacagcagttcttttgctttcgcaac (46) | APTA |
| yy147(SphI) | gggaaagcatgcaggagatataccatgaattatcagaacgacgatttacgc (47) | To amplify aroG$^{fbr}$ for |
| yy148(HindIII) | gggaaaaagctttttacccgcgacgcgcttttac (48) | pCS-APTA |
| yy303(SacI) | gggaaagagctctcttcacctcgagaattgtgagcg (49) | To amplify APTA operon |
| yy304(SpeI) | gggaaaactagtctactcaggagagcgttcaccg (50) | for pZE-EP-APTA |
| yy295(KpnI) | gggaaaggtaccatgagtctgaatttccttgattttgaacagc (51) | To amplify accA for pSA- |
| yy296(PstI) | gggaaactgcagttacgcgtaaccgtagctcatcag (52) | ACCB |
| yy297(PstI) | gggaaactgcagaggagatataccatgctggattgaacgaattaaagc (53) | To amplify accD for pSA- |
| yy298(SalI) | gggaaagtcgactcaggcctcaggttcctgatc (54) | ACCB |

TABLE 3-continued

Primers used as described herein.

| Primer | Sequence (SEQ ID NO) | Use |
| --- | --- | --- |
| yy299(SalI) | gggaaagtcgacaggagatataccatggatattcgtaagattaaaaaactgatcgag (55) | To amplify accBC for pSA-ACCB |
| yy300(EcoRI) | gggaaagaattcttattttttcctgaagaccgagttttttctcc (56) | |
| yy301(EcoRI) | gggaaagaattcaggagatataccatgaaggataacaccgtgccac (57) | To amplify birA for pSA-ACCB |
| yy302(BamHI) | gggaaaggatccttattttttctgcactacgcagggatatttc (58) | |

Enzyme Assays of SCLs.

To evaluate the activity of SCLs (SdgA and MdpB2), the *E. coli* strain BL21 Star™ (DE3) was transformed with pET-SdgA and pET-MdpB2 separately. The obtained transformants were pre-inoculated in Luria-Bertani (LB) medium containing 100 µg/ml of ampicillin and grown aerobically at 37° C. overnight. Next day, the pre-inoculums were transferred into 50 ml of fresh LB medium at a volume ratio of 1:100. The cultures were left to grow at 37° C. till the $OD_{600}$ values reached 0.6-0.8 and then induced with 1.0 mM IPTG. Protein expression was conducted at 30° C. for another 5 h. The cells were harvested and the proteins were purified with the His-Spin Protein Miniprep™ kit (ZYMO RESEARCH). The BCA kit (Pierce Chemicals) was used to estimate protein concentrations. The SCL enzyme assays were performed according to the method described by Ishiyama et al. with modifications (Ishiyama et al. *Appl. Environ. Microbiol.* 70, 1297-1306 (2004)). The 1 ml reaction system contained 785 µl of Tris-HCl (pH=7.5, 100 mM), 5 µl of the purified enzyme (SdgA or MdpB2), 10 µl of $MgCl_2$ (0.5 M), 50 µl of ATP (100 mM), 50 µl of coenzyme A (5 mM), 100 µl of salicylate (100 µM, 200 µM, 500 µM, 1 mM). The reactions lasted 0.5 min for SdgA and 2.5 min for MdpB2, respectively, and then were terminated by acidification with 20 µL of HCl (20%). The reaction rates were calculated according to the salicylate consumption at 30° C., which was measured by HPLC.

Enzyme Assays of ICSs.

The kinetic parameters of the ICSs: EntC, MenF, and PchA were determined using coupled assays (Payne et al. *Org. Biomol. Chem.* 7, 2421-2429 (2009)). IPL from *P. aeruginosa* (PaPchB) was used to convert isochorismate to salicylate which was quantified by HPLC. The 1 ml reaction system contained 866 µl of Tris-HCl (pH=7.5, 100 mM), 20 µl of $MgCl_2$ (0.5 M), 0.1 µM of purified ICS (EntC, MenF, or PchA), 0.5 µM of purified PaPchB, 100 µl of chorismic acid (100 µM, 200 µM, 500 µM, 1 mM). The reactions lasted 1 min for EntC, and 5 min for MenF and PchA, respectively, and then were terminated by acidification with 20 µL of HCl (20%). The reaction rates were calculated according to the salicylate accumulation at 30° C. The kinetic parameters were estimated by using OriginPro8 through non-linear regression of the Michaelis-Menten equation.

Coupled Enzyme Assays for IPLs.

First, purified enzyme EntC was used to convert an excess amount of chorismic acid into IPL's substrate isochorismate. The 1 ml reaction system containing Tris-HCl (100 mM, pH=7.5), $MgCl_2$ (5 mM), purified EntC (0.5 µM), Chorismic acid (100 µM) was incubated at 30° C. for 30 min. Then the purified PaPchB or PfPchB was added into the reaction system and incubated for 30 seconds, after which the reactions were terminated by acidification with 20 µl of HCl (20%). The enzyme turnover numbers were estimated according to the generation of salicylate, which was measured by HPLC.

Feeding Experiments.

Feeding experiments were conducted to examine the conversion of salicylate to 4HC. The *E. coli* strain carrying pZE-BIS3-SdgA or pZE-PS was inoculated in 3 ml LB medium and grown overnight at 37° C. Subsequently, 200 µl overnight cultures were re-inoculated into 20 ml of M9Y medium and grown at 37° C. with shaking (250 rpm). The expression of the enzymes was induced by adding IPTG to a final concentration of 0.5 mM when the $OD_{600}$ values reached 0.6-0.7. At the same time, 1 mM of salicylate was added into the cultures and the cultures were shaken at 30° C. for several hours, which was followed by HPLC analysis.

De Novo Biosynthesis of Salicylate and 4HC.

Overnight cultures (100 µl) of salicylate or 4HC producing strains were inoculated into M9Y medium (10 ml) containing appropriate antibiotics and cultivated at 37° C. with shaking at 300 rpm. When the $OD_{600}$ values of the cultures reached around 0.6, IPTG was added to the cultures to a final concentration of 0.5 mM. Then the cultures were transferred to 30° C. for salicylate and 4HC biosynthesis. Samples were taken every other hour and analyzed by HPLC.

In Vitro Complementation Assay.

The *E. coli* strain carrying the plasmid pZE-EPBS was pre-inoculated into 3 ml LB liquid medium containing 100 µg/ml of ampicillin and grown at 37° C. overnight with shaking at 300 rpm. In the following day, 1 ml of the preinoculum was added to 50 ml of fresh M9Y medium. The culture was left to grow at 37° C. till the $OD_{600}$ value reached around 0.6 and then induced with 0.5 mM IPTG. The expression of the pathway enzymes was conducted at 30° C. for another 5 hours. The cells were harvested and re-suspended in 2 ml of Tris-HCl buffer (100 mM, pH=7.5), and then lysed by French Press. The soluble fraction was collected by ultra-centrifugation and used as the crude enzyme extract for the complementation assay. The 1 ml reaction system firstly contained Tris-HCl (100 mM, pH=7.5), $MgCl_2$ (5 mM), ATP (5 mM), coenzyme A (0.25 mM), salicylate (0.2 mM), crude extract (50 µl) with/without purified SdgA (20 µl). After 30 min reaction, 100 µl of malonyl-CoA (2 mM) and 50 µl of crude extract with/without purified BIS3 (20 µl) were supplemented into the reaction system. The reactions were finally terminated in another 0.5-2 h by acidification. The reaction rates were calculated according to the generation of 4HC that was measured by HPLC. The protein concentrations of purified BIS3 and SdgA were 1200 and 395 mg/L, respectively.

Semi-Synthesis of Warfarin.

The culture containing about 500 mg/L of produced 4HC was centrifuged to remove the cells. Then 1 g/L of benzyldeneacetone and 100 mg/L of catalyst (S,S)-1,2-diphenylethylenediamine were added into the supernatant followed by incubation in the sonication bath for 3 hours. The production of warfarin was analyzed by HPLC.

HPLC Quantitative Analysis.

4-Hydroxycoumarin (from ACROS ORGANICS), salicylate (from ACROS ORGANICS), and warfarin (from MP Biomedicals) were purchased as the standards. Both the standards and samples were quantitatively analyzed by HPLC (Dionex Ultimate 3000) with a reverse-phase ZORBAX SB-C18 column and an Ultimate 3000 Photodiode Array Detector. Solvent A was sodium acetate solution (20 mM, pH=5.5), and solvent B was 100% methanol. The following gradient was used for 4HC and salicylate analysis at a flow rate of 1 ml/min: 5 to 50% solvent B for 15 min, 50 to 5% solvent B for 1 min, and 5% solvent B for additional 4 min, For warfarin analysis, the gradient was from 20% to 80% solvent B. Quantification was based on the peak areas referring to the commercial standards at the wavelength of 285 nm. Samples containing over 200 mg/L of products were diluted before running HPLC to maintain a linear concentration-peak area relationship.

ESI-MS and NMR Analysis.

Figure 10:
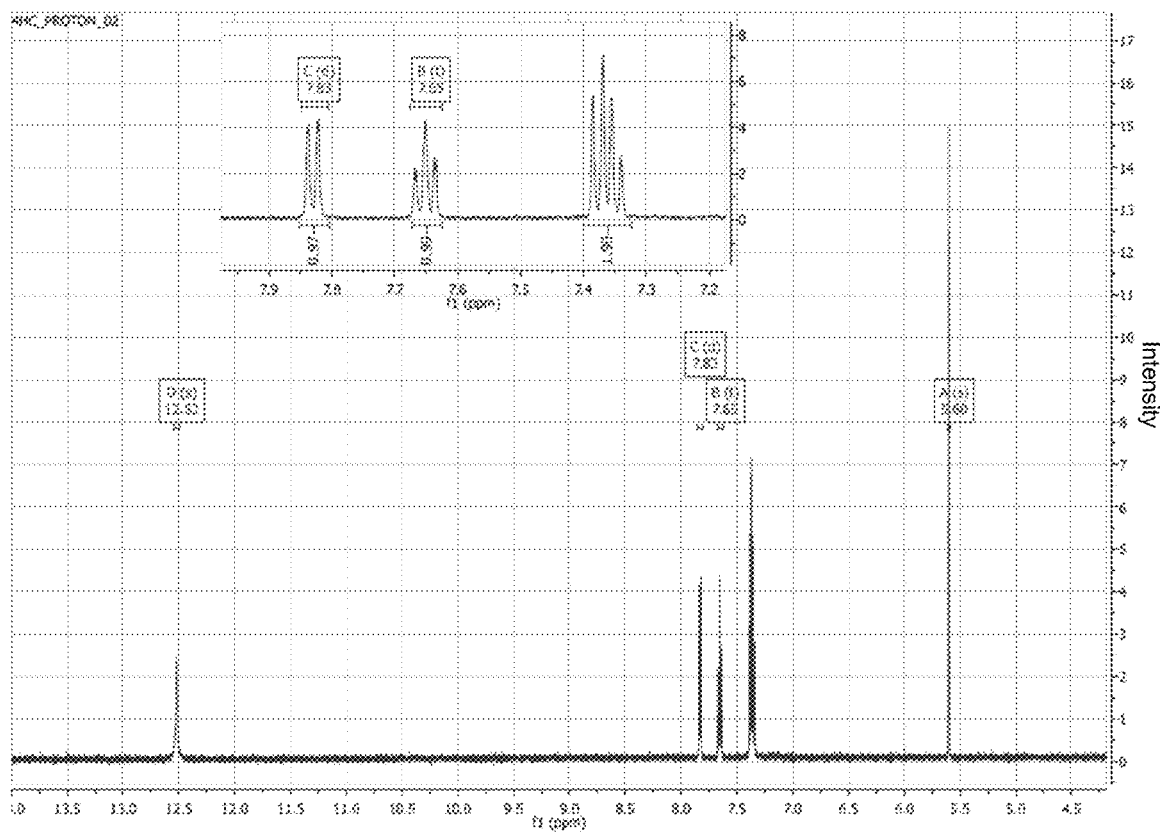
FIG. 10. $^1$H NMR spectrum of the biosynthesized 4HC. The multiplet between 7.34 and 7.39 was determined to be the signal of two protons based on its integration value and the subsequent gHSQC spectrum FIG. 11. $^{13}$C NMR spectrum of the biosynthesized 4HC. The arrow indicates the solvent DMSO as the reference compound.
Figure 11:
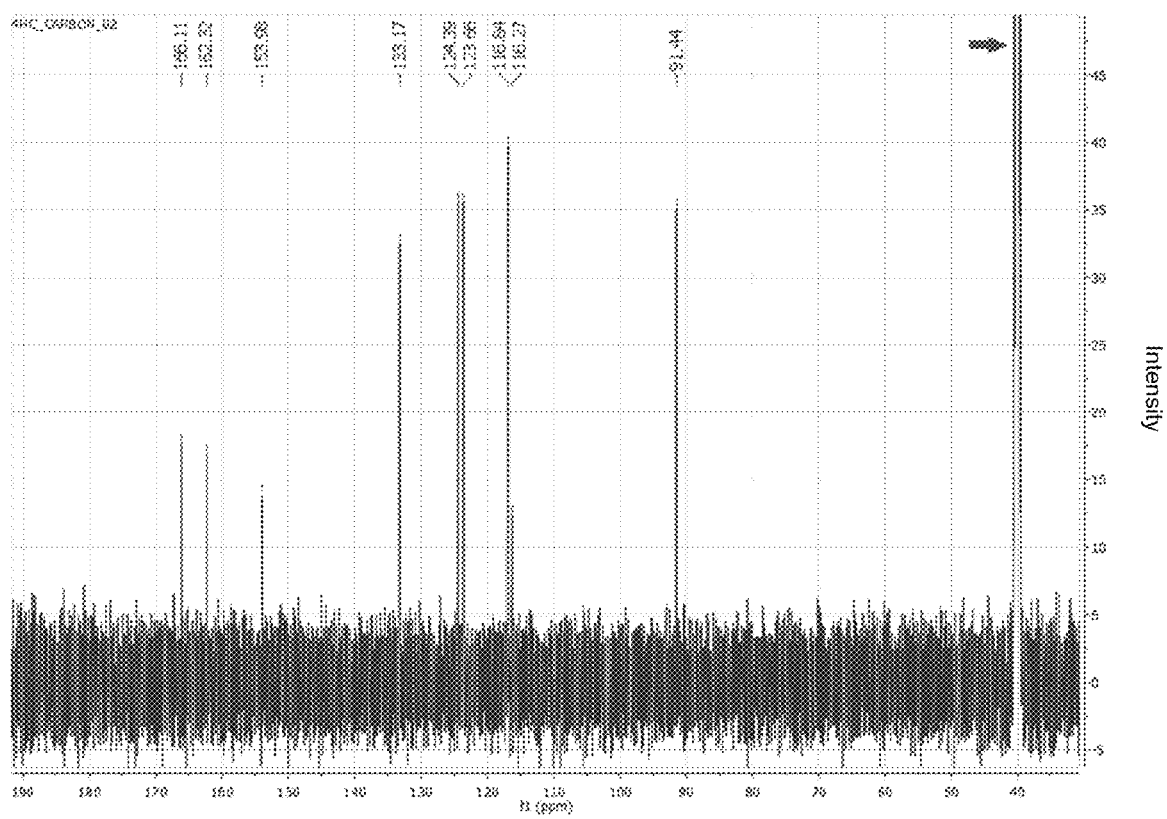
Figure 12:
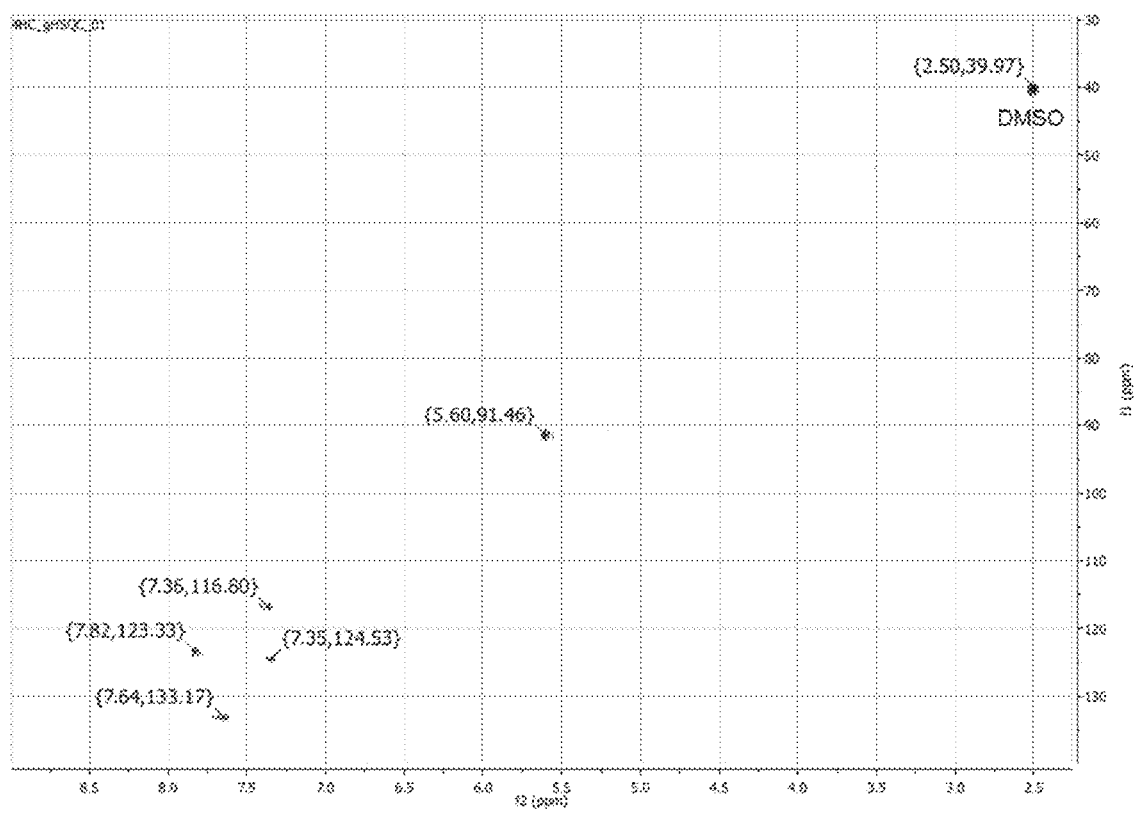
FIG. 12. gHSQC (gradient Heteronuclear Single Quantum Coherence) NMR spectrum of the biosynthesized 4HC. f1 indicates chemical shift for carbon; f2 indicates chemical shift for proton.
Figure 16:
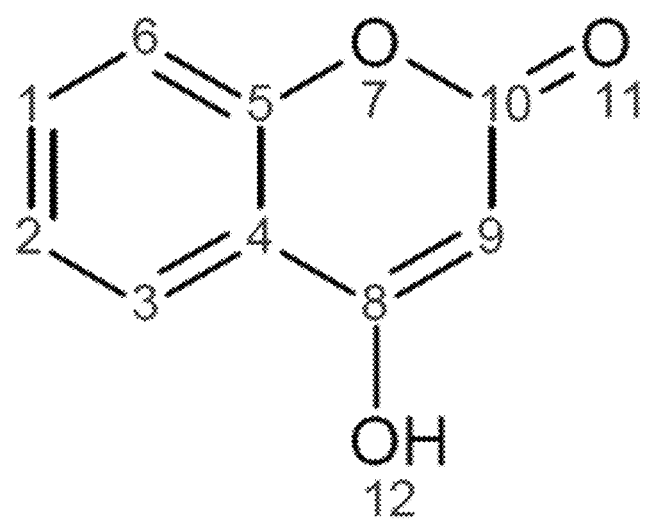
FIG. 16. Numbering of the assigned carbons and protons. The numbers indicate the carbons and protons in the NMR data.

For ESI-MS analysis, the peak corresponding to 4HC was collected from HPLC, extracted with acetyl acetate, and dissolved in $H_2O$. ESI-MS analysis was conducted using the Perkin Elmer Sciex API I plus mass spectrometer. For NMR analysis, the biosynthesized 4HC was extracted from the culture with the same volume of acetyl acetate. Then the extract was dried by a vacuum evaporator, dissolved with DMSO, and diluted with water. Further purification was performed by collecting the 4HC fraction from HPLC. The collected fraction was extracted again with acetyl acetate, dried, and re-dissolved in DMSO. Then the purified 4HC (roughly 0.2-0.3 mg in around 50 μl DMSO) was diluted in 600 μl DMSO-d6. The NMR analysis was conducted using 500-MHz Varian Unity Inova with a 5 mm Broad Band Detection Probe at 25° C. The solvent DMSO was used as the reference compound. $^1H$, $^{13}C$, and gHSQC (gradient Heteronuclear Single Quantum Coherence) analysis were conducted (FIGS. 10-12). The carbons and protons were assigned by referring to the data from Spectral Database for Organic Compounds (SDBS No.: 6281) (FIG. 16).

Results

Retro-Design of 4HC Biosynthesis.

Figure 1:
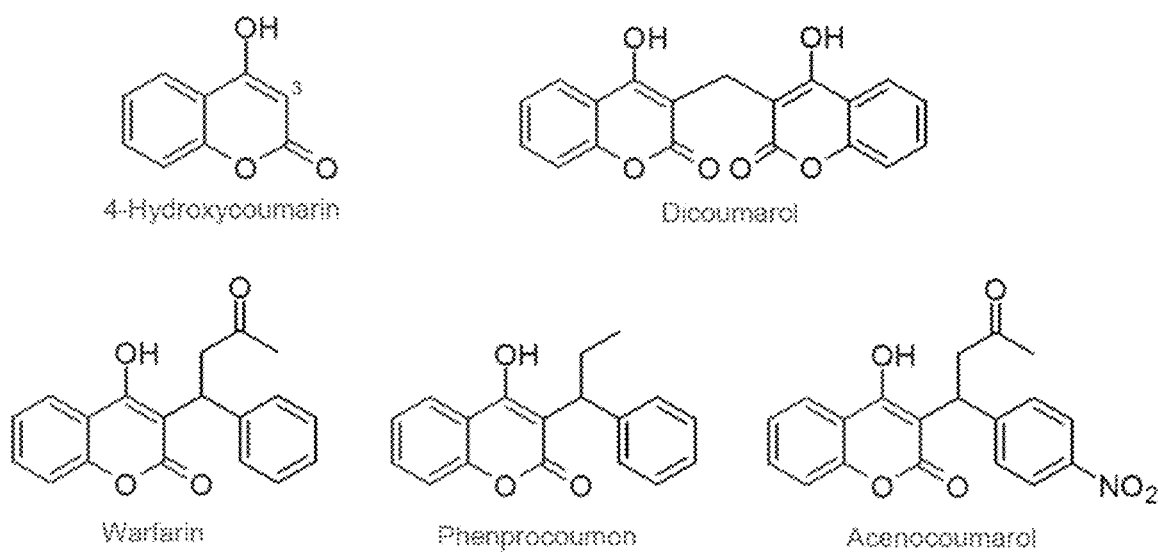
FIG. 1. Molecular structures of 4-hydroxycoumarin (4HC) class anticoagulants. Dicoumarol is a natural 4HC derivative and served as the earliest anticoagulant; while warfarin, phenprocoumon, and acenocoumarol are the most widely prescribed synthetic 4HC anticoagulants. These compounds share the 4HC core structure but differ in substitution at 3-position on the pyrone ring.

4HC is a direct precursor of natural and synthetic anticoagulants (FIG. 1). Its biosynthesis has not been fully understood as mentioned above (FIG. 2A). However, identification of the 4HC-forming reaction catalyzed by BIS provided an opportunity to explore the combinatorial biosynthesis of 4HC. The design was firstly focused on the establishment of a reaction that can provide the substrate salicoyl-CoA for BIS. We speculated that esterification of salicylate with coenzyme A is a reaction that might be catalyzed by certain CoA transferase/ligase. By searching the enzyme database (BRENDA) and literature, we found only a few enzymes with salicylate:CoA ligase (SCL) activity, including SdgA (involved in salicylate degradation in *Streptomyces* sp. WA46), MdpB2 and SsfL1 (involved in maduropeptin and tetracycline SF2575 biosynthesis in *Actinomadura madurae* ATCC39144 and *Streptomyces* sp. SF2575, respectively) (Ishiyama et al. *J. Appl. Environ. Microbiol.* 70, 1297-1306 (2004)), (Ling et al. *J. Am. Chem. Soc.* 132, 12534-12536 (2010)), (Pickens et al. *J. Am. Chem. Soc.* 131, 17677-17689 (2009)). Besides, some benzoate:CoA ligases also exhibited weak side activity towards salicylate (Geissler et al. *J. Bacteriol.* 170, 1709-1714 (1988)), (Beuerle et al. *Arch. Biochem. Biophys.* 400, 258-264 (2002)). To further achieve de novo biosynthesis of 4HC, a metabolic connection has to be established between salicylate and the host's metabolism. In nature, salicylate is produced not only by plants as a signal molecule but also by some bacteria as an intermediate in siderophore biosynthesis (Gaille et al. *J. Biol. Chem.* 277, 21768-21775 (2002)), (Nagachar et al. *FEMS Microbiol. Lett.* 308, 159-165 (2010). Compared with the intricate plant pathways, bacteria generate salicylate using more straightforward strategies. For instance, in *Pseudomonas* and *Mycobacterium* species, salicylate formation requires only two enzymes that are isochorismate synthase (ICS) and isochorismate pyruvate lyase (IPL) by shunting chorismate from shikimate pathway (Gaille et al. *J. Biol. Chem.* 277, 21768-21775 (2002)), (Nagachar et al. FEMS Microbiol. Lett. 308, 159-165 (2010)). Taken together, a novel biosynthetic mechanism for 4HC was established by grafting the enzymatic reactions catalyzed by ICS, IPL, SCL, and BIS onto the shikimate pathway (FIG. 2B).

Conversion of Salicylate to 4HC.

Figure 3:
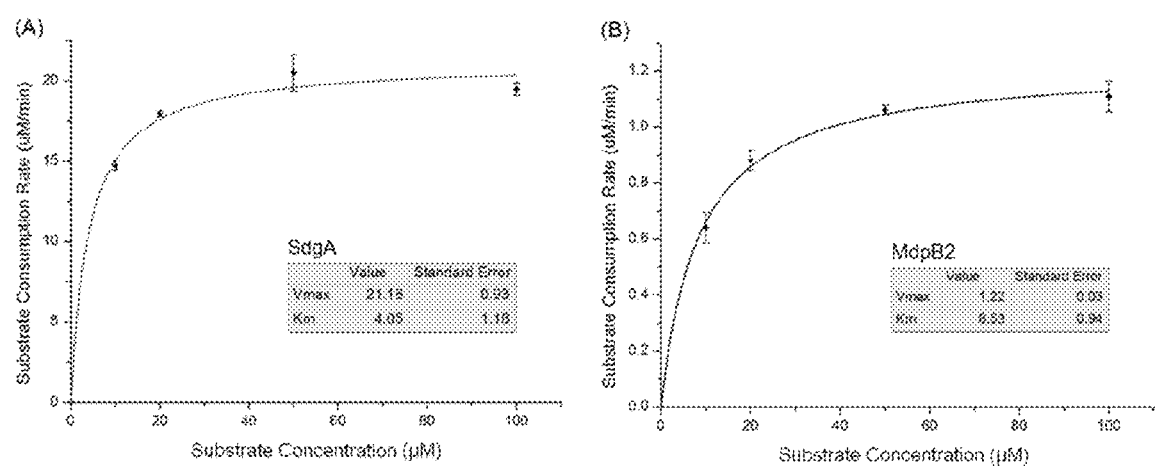
FIG. 3. Kinetic parameters of SdgA (A) and MdpB2 (B). The $K_m$ and $V_{max}$ values were estimated with OriginPro8 through non-linear regression of the Michaelis-Menten equation. Protein concentrations [E] of SdgA and MdpB2 in the reaction systems were 0.0332 µM and 0.0172 µM, respectively. $k_{cat}$ values of the two enzymes were calculated according to the formula $k_{cat}=V_{max}/[E]$. All data points are reported as mean±s.d. from two independent experiments (n=2). Error bars are defined as s.d.
Figure 4:
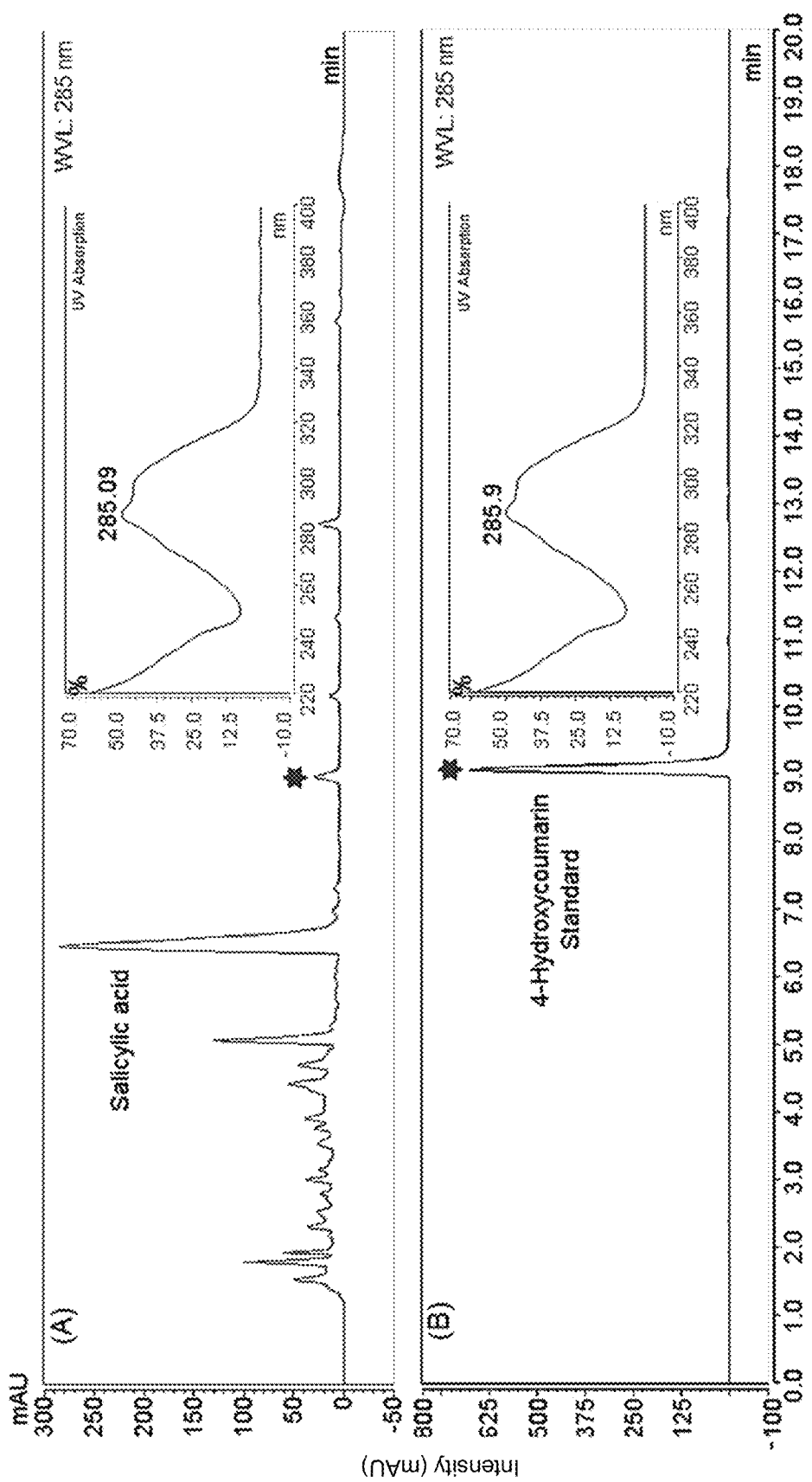
FIG. 4. HPLC analysis of 4HC produced by E. coli carrying pZE-BIS3-SdgA in the presence of 1 mM of salicylic acid. (A) A sample taken from the cell culture after 24 hours. (B) 50 mg/L of 4HC standard. The retention time was about 9.0 min. UV absorbance profiles are shown beside the peaks marked with red-colored asterisks.

Conversion of salicylate to 4HC (the lower module) by SCL and BIS is a non-natural pathway. The three identified BISs were reported to show different preferences towards salicoyl-CoA; BIS3 was selected for pathway construction due to its higher $k_{cat}$ value (Liu et al. *Plant Mol. Biol.* 72, 17-25 (2010)). To obtain an optimal SCL, we measured the catalytic parameters of SdgA and MdpB2 after evaluating all the reported SCLs. The enzyme assays revealed that SdgA ($K_m$=4.05 μM, $k_{cat}$=10.63 $s^{-1}$) possesses about 2-fold higher substrate affinity and 10-fold higher activity than MdpB2 ($K_m$=8.53 μM, $k_{cat}$=1.18 $s^{-1}$) (FIG. 3 and Table 4). To further test their biosynthetic potential in vivo, an expression vector (pZE-BIS3-SdgA) carrying the genes of BIS3 and SdgA was constructed and introduced into *E. coli*. The strain was cultured in the presence of 1 mM salicylate for 24 hours. HPLC analysis showed that the strain produced 2.3±0.2 mg/L of 4HC with around 3-6 mg/L salicylate consumed (FIG. 4).

TABLE 4

Kinetic parameters of the enzymes measured as described herein.

| | Kinetic Parameters* | | |
|---|---|---|---|
| Enzyme | $K_m$ (μM) | $k_{cat}$ ($S^{-1}$) | $k_{cat}/k_m$ ($S^{-1} M^{-1}$) |
| SdgA | 4.05 ± 1.18 | 10.63 ± 0.48 | 2624691 |
| MdpB2 | 8.53 ± 0.94 | 1.18 ± 0.03 | 138335 |
| EntC | 11.93 ± 1.37 | 2.12 ± 0.07 | 177703 |
| MenF | 6.75 ± 2.99 | 0.13 ± 0.01 | 19259 |
| PchA | 3.69 ± 0.53 | 0.20 ± 0.01 | 54201 |

*All data are reported as mean ± s.d. from two independent experiments (n = 2).

Biosynthesis of Salicylate.

Figure 5:
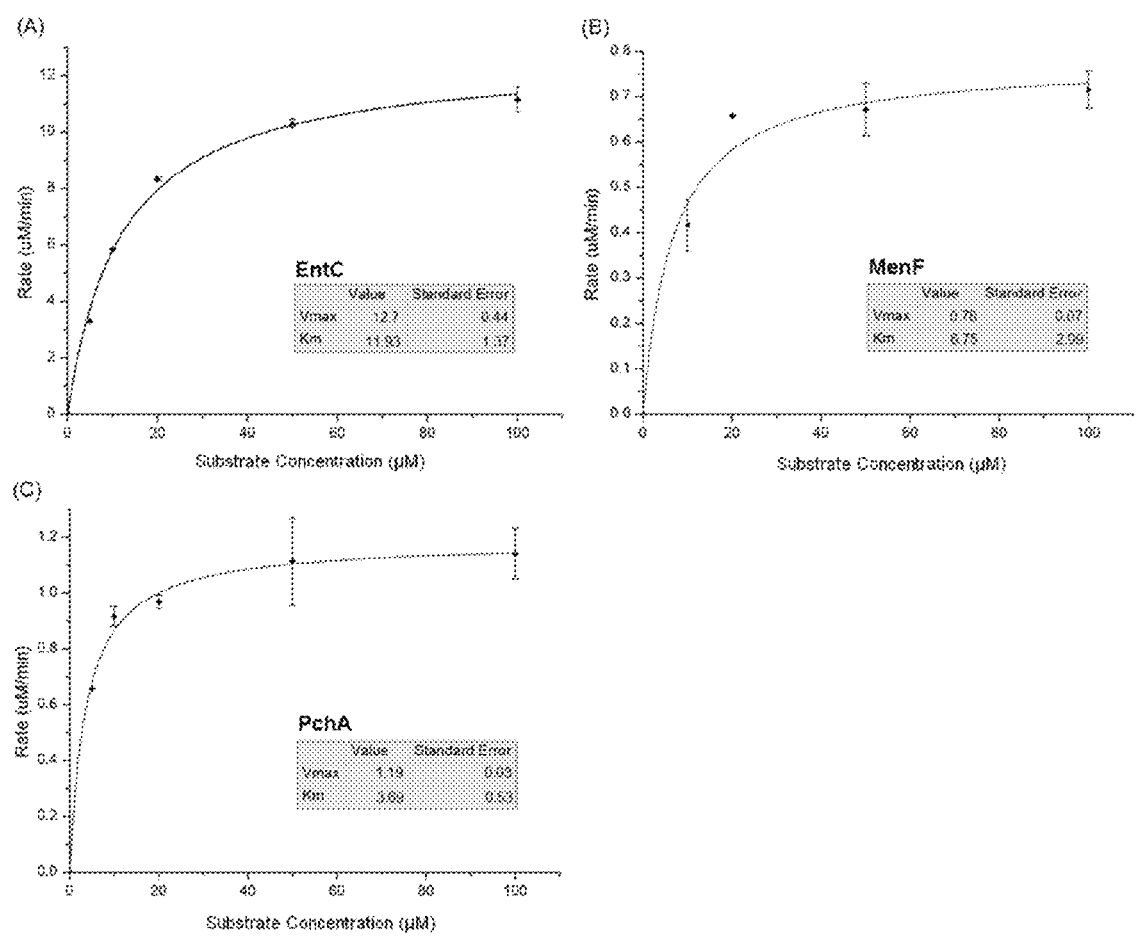
FIG. 5. Kinetic parameters of EntC (A), MenF (B), and PchA (C). The $K_m$ and $V_{max}$ were generated with OriginPro8 through non-linear regression of the Michaelis-Menten equation. Protein concentrations [E] of EntC, MenF, and PchA in the reaction systems were all 0.1 µM, respectively. $k_{cat}$ of the enzymes were calculated according to the formula $k_{cat}V_{max}/[E]$. All data points are reported as mean±s.d. from two independent experiments (n=2). Error bars are defined as s.d.
Figure 6:
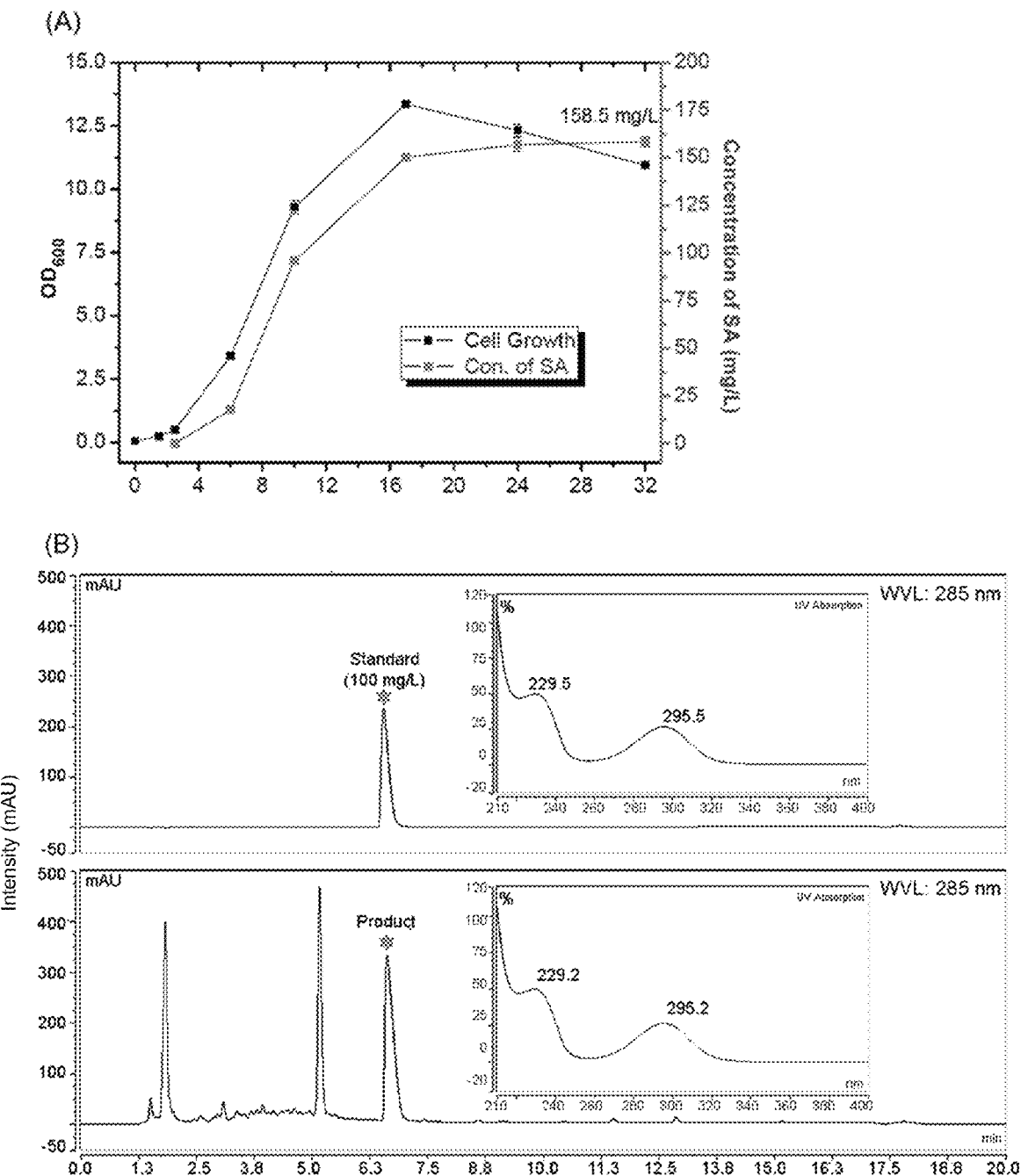
FIG. 6. Salicylate biosynthesis in E. coli and HPLC analysis. (A) Time courses of cell growth and salicylate biosynthesis for E. coli carrying pZE-EP. All data points are reported as mean±s.d. from three independent experiments (n=3). Error bars are defined as s.d. (B) HPLC analysis of the biosynthesized salicylate. The UV absorption profiles of the standard and the biosynthesized salicylate are shown beside their peaks (indicated by asterisks).

We borrowed the biosynthetic strategy from *Pseudomonas* involving ICS and IPL to establish the salicylate biosynthesis (the upper module) in *E. coli*. First, to screen for a potent ICS, the enzymes PchA (from *P. aeruginosa*), EntC, and MenF (from *E. coli*) were overexpressed and purified for enzyme kinetic studies. The enzyme assays indicated that EntC ($K_m$=11.93 μM and $k_{cat}$=2.12 $s^{-1}$) is much more active than MenF ($K_m$=6.75 μM and $k_{cat}$=0.13 $s^{-1}$) and PchA ($K_m$=3.69 μM and $k_{cat}$=0.20 $s^{-1}$) (FIG. 5 and Table 4). Then the activity of IPLs from *Pseudomonas fluorescence* and *P. aeruginosa* were estimated by coupled enzyme assays since the substrate isochorismate is neither commercially available nor chemically stable. The results showed that the former enzyme (PfPchB, estimated turnover number=15.8 $s^{-1}$) is slightly more active than the latter one (PaPchB, estimated turnover number=11.2 $s^{-1}$). Therefore, EntC and PfPchB were selected for the test of salicylate biosynthesis in vivo. We consecutively cloned the genes of EntC and PfPchB into the vector pZE12-luc as an operon, generating pZE-EP. As we expected, *E. coli* strain harboring pZE-EP obtained the capability to produce salicylate. By the end of 32 h, 158.5±2.5 mg/L of salicylate was accumulated in the cultures following a growth-dependent production pattern (FIG. 6).

Validation and Diagnosis of the 4HC Biosynthetic Mechanism.

With the validated upper and lower modules, further efforts were directed to the validation of the complete 4HC biosynthetic mechanism. The genes encoding EntC, PfPchB, BIS3, and SdgA were consecutively cloned into the vector pZE12-luc as an operon, generating a plasmid pZE-EPBS. However, the E. coli strain harboring pZE-EPBS only produced a trace amount of 4HC (<0.2 mg/L), but accumulated a large amount of salicylate (156.2±18.7 mg/L) after 48 h production in shake flasks. The result suggested that the upper module performed well in the full pathway; while the bottleneck was in the lower module.

Figure 7:
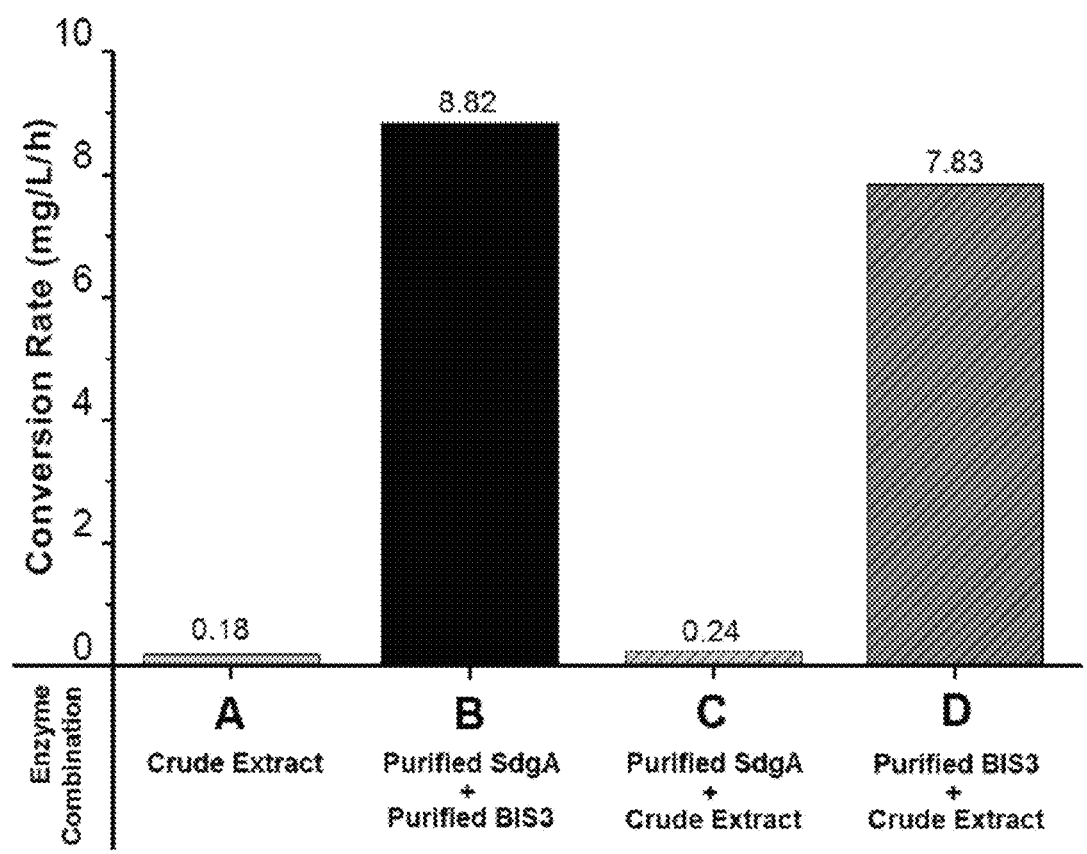
FIG. 7. In vitro complementation assay for examining the rate-limiting enzyme. 4 combinations of enzymes were tested for in vitro 4HC formation. *Crude Extract was prepared from the lysed cells of the E. coli strain expressing the full pathway (E. coli/pZE-EPBS).

To locate the rate-limiting step, we designed and performed an in vitro complementation assay in which excess amounts of purified SdgA and/or BIS3 were supplemented into the crude extract of the E. coli cells expressing the full pathway. As shown in FIG. 7, without supplemented enzymes, the crude extract can only convert salicylate to 4HC at a very low rate (0.18 mg/L/h) in the presence of required cofactors; while the presence of purified SdgA and BIS3 significantly improved the rate (8.82 mg/L/h), indicating that the purified enzymes functioned well in this assay system (positive control). When purified SdgA was supplemented alone into the crude extract, the conversion rate was not obviously increased (0.24 mg/L/h). Noticeably, when purified BIS3 was added alone, the 4HC formation was recovered to a rate (7.83 mg/L/h) comparable with that of the positive control, indicating that BIS3 was a major bottleneck in the pathway. We speculated that the low in vivo activity of BIS3 might result from the slow kinetics, sub-optimal expression, instability, or cross-species incompatibility issues. To overcome this bottleneck, searching for a superior substitute was our first choice.

Bioprospecting for a Superior Substitute to BIS.

Figure 8:
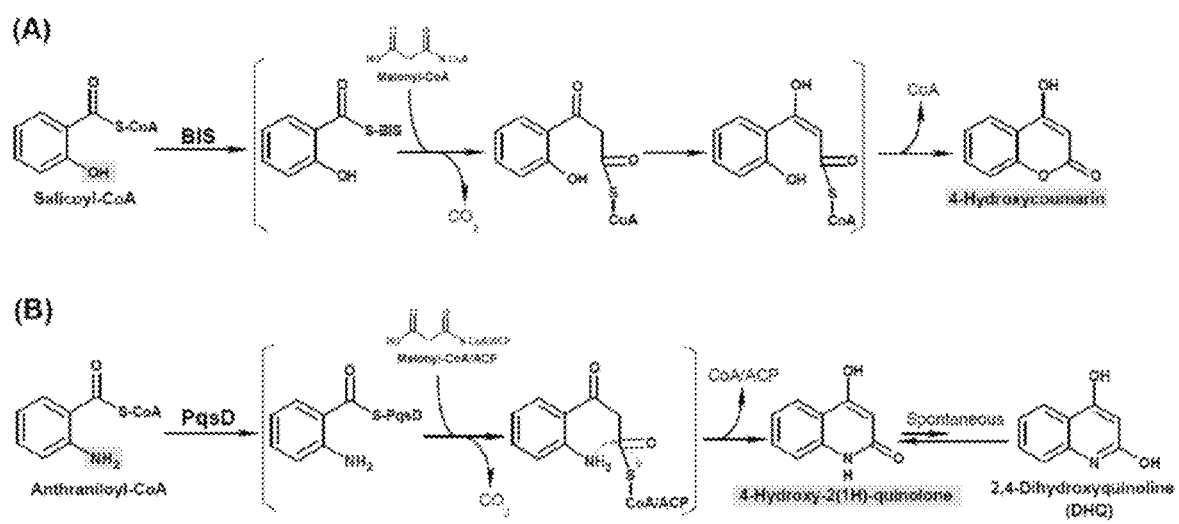
FIG. 8. Comparison of the reaction mechanisms of biphenyl synthase (BIS) and Pseudomonas quinolone synthase (PqsD). BIS catalyzes the decarboxylative condensation of malonyl-CoA with salicoyl-CoA, after which intramolecular cyclization takes place to form 4HC. PqsD was reported to condense malonyl-CoA/malonyl-ACP and anthraniloyl-CoA. Then similar intramolecular cyclization takes place to form 4-hydroxy-2(1H)-quinolone which is spontaneously interchangeable to its tautomer 2,4-dihydroxyquinoline (DHQ). Under physiological conditions 4-hydroxy-2(1H)-quinolone is the dominant form.
Figure 9:
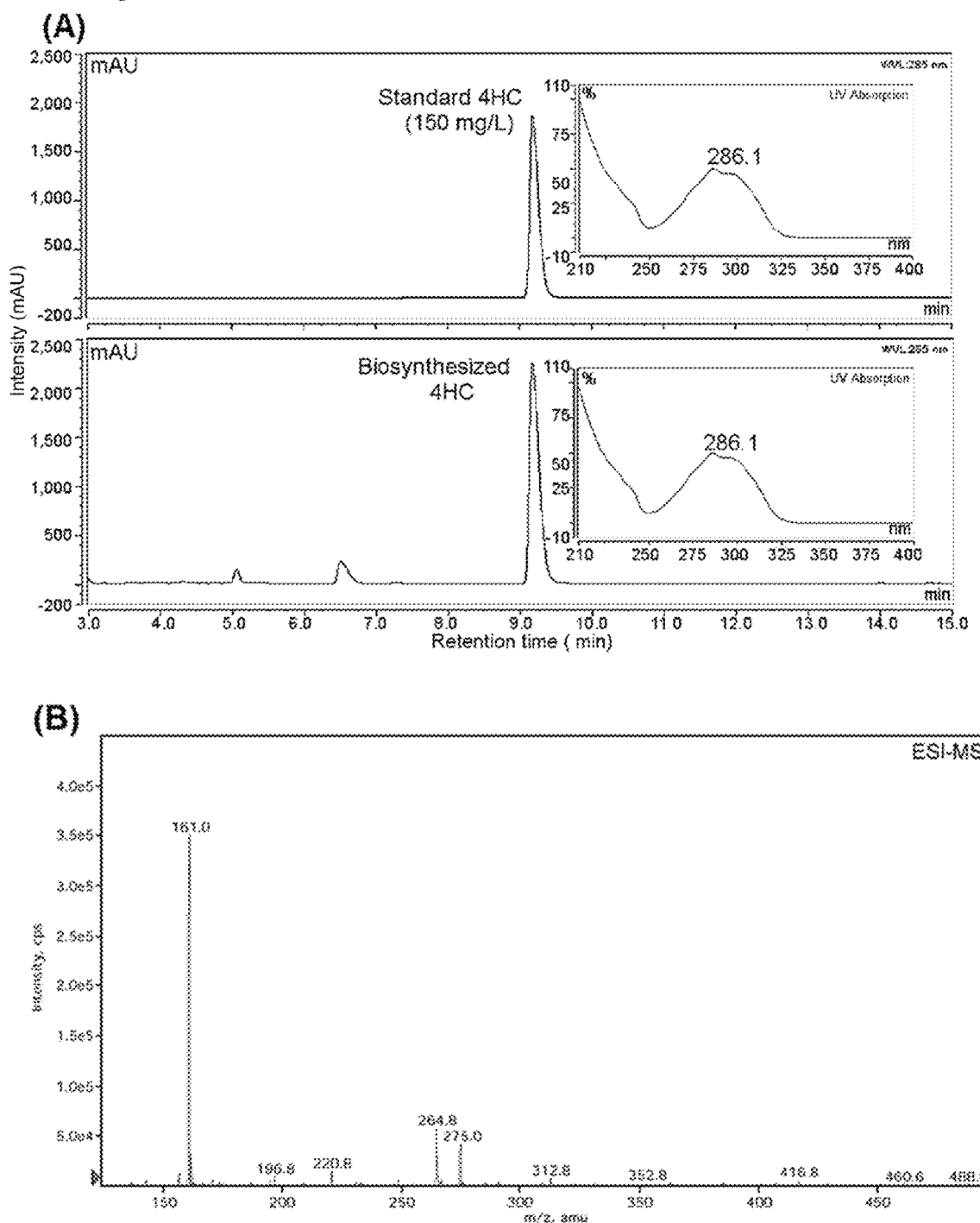
FIG. 9. HPLC and ESI-MS analysis of the biosynthesized 4HC. (A) HPLC analysis of the biosynthesized 4HC. The UV absorption profiles of the standard and the biosynthesized 4HC are shown beside their peaks. (B) ESI-MS (negative ion mode) analysis of the biosynthesized 4HC collected and purified by HPLC. The peak at 161 (M-H)— corresponds to the molecular weight 162 (molecular formula $C_9H_6O_3$).

BIS is a subclass of chalcone synthase (CHS)-like type III polyketide synthases (PKS). However, no other type III PKS with sequence similarity has been identified to catalyze the 4HC-forming reaction. By structure-based examination of bacterial secondary metabolites, we identified that 4-hydroxy-2(1H)-quinolone in P. aeruginosa shares high structural similarity with 4HC (Zhang et al. J. Biol. Chem. 283, 28788-28794 (2008)). The formation of 4-hydroxy-2(1H)-quinolone is catalyzed by a β-ketoacyl-ACP synthase III (FabH)-type quinolone synthase (PqsD) via decarboxylative condensation of malonyl-CoA or -ACP with anthraniloyl-CoA and spontaneous intramolecular cyclization (Zhang et al. J. Biol. Chem. 283, 28788-28794 (2008)), Bera et al. Biochemistry (Most.) 48, 8644-8655 (2009)). Despite having a tautomer 2,4-dihydroxyquinoline (DHQ), 4-hydroxy-2 (1H)-quinolone is the predominant form at physiological pH (Heeb et al. FEMS Microbiol. Rev. 35, 247-274 (2011)) (FIG. 8B). We reasoned that PqsD may also accept salicoyl-CoA as a substrate to form 4HC, as BIS does (FIG. 8A). To test this hypothesis, we replaced the BIS3 gene with PqsD coding sequence in the lower module, generating the plasmid pZE-PqsD-SdgA (pZE-PS). The E. coli strain carrying pZE-PS completely converted 2 mM of salicylate (276 mg/L) into 4HC within about 7 h with a yield of over 99%, indicating the high activity of PqsD towards salicoyl-CoA. The produced 4HC has identical HPLC retention time and UV absorption profile with its commercial standard. Its identity was further confirmed by ESI-MS and NMR analysis (FIGS. 9-12 and Table 5).

TABLE 5

NMR data of 4HC

| Atom | Chemical Shift (ppm) | Splitting Pattern | J-Value (Hz) |
|---|---|---|---|
| 1 C | 133.17 | | |
| H | 7.65 | t | 7.8 |
| 2 C | 124.39 | | |
| H | 7.35 | t* | 7.9 |
| 3 C | 123.66 | | |
| H | 7.83 | d | 7.8 |
| 4 C | 116.27 | | |
| 5 C | 153.98 | | |
| 6 C | 116.84 | | |
| H | 7.37 | d* | ND |
| 7 O | | | |
| 8 C | 162.32 | | |
| 9 C | 91.44 | | |
| H | 5.60 | s | |
| 10 C | 166.11 | | |
| 11 O | | | |
| 12 O | | | |
| H | 12.52 | s, br | | s: singlet;
d: doublet;
t: triplet;
br: broad peak;
ND: not determined due to the overlap.
*The multiplet between 7.34 and 7.39 was determined as the overlap of a triplet and a doublet based on the gHSQC spectrum and previously reported data.

Metabolic Engineering for Improved 4HC Biosynthesis.

Figure 13:
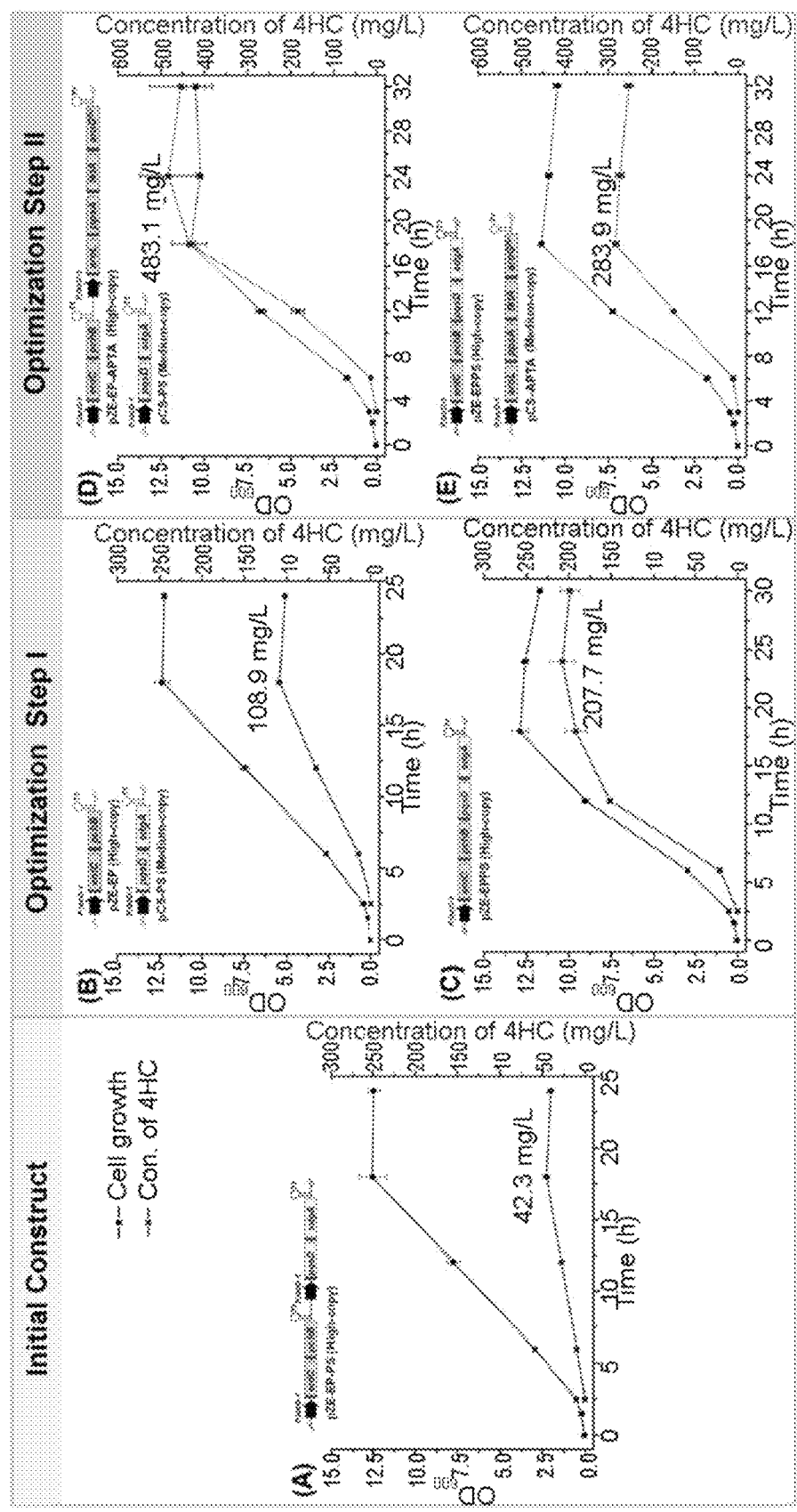
FIG. 13. Growth and production profiles of the constructed 4HC producing E. coli strains. (A) Strain A (E. coli carrying pZE-EP-PS) expresses the upper module (EP) and lower module (PS) with 2 operons on the high-copy plasmid; (B) and (C) indicate the modular optimization by adjusting gene organization, copy number, and operon configuration. Strain B separately expresses upper module (EP) and lower module (PS) on the high-copy and the medium-copy plasmids, respectively, while Strain C expresses the full pathway within the same operon on the high-copy plasmid; (D) and (E) indicate improving precursor availability by over-expressing aroL, ppsA, tktA, and aroG$^{fbr}$ (APTA) on the high-copy and medium-copy plasmids, respectively. Characteristics of the plasmid(s) carried by E. coli are shown on the upper-left corner of each graph. All data are reported as mean±s.d. from three independent experiments (n=3). Error bars are defined as s.d.

We first reconstituted the improved biosynthetic mechanism in E. coli by introducing the two modules as dual operons using the high-copy plasmid pZE-EP-PS. The E. coli strain carrying pZE-EP-PS (Strain A, FIG. 13A) produced 42.3 mg/L of 4HC without addition of any intermediates. Meanwhile, a trace amount of salicylate was detected in the cultures, indicating that the lower module functioned well with this expression strategy and almost completely converted endogenous salicylate to 4HC. However, this expression strategy decreased the efficiency of the upper module. According to the stoichiometry, 42.3 mg/L of 4HC should be generated from 36.1 mg/L salicylate which is much less than the production obtained with the E. coli strain only expressing the upper module (pZE-EP). We speculated that the decrease in salicylate-producing capability might be attributed to the following two reasons: 1) the two adjacent operons on the same plasmid might interfere with each other; 2) the incongruous expression of the upper and lower modules may have caused metabolic imbalance. To test this hypothesis, we co-expressed the lower module operon (PqsD-SdgA) using a medium-copy plasmid (pCS-PS) together with pZE-EP in E. coli (Strain B, FIG. 13B). Strain B produced 108.9 mg/L 4HC in 18 hours with no measurable salicylate accumulated. Furthermore, we explored the performance of another construct pZE-EPPS in which the genes encoding the full pathway enzymes were consecutively cloned as one operon. E. coli harboring pZE-EPPS (Strain C, FIG. 13C) produced 207.7 mg/L 4HC in 24 h with 21.6 mg/L salicylate left unconverted. With this expression strategy, the production of 4HC was improved by 5 folds compared with the initial construct, suggesting that gene organization and operon configuration may influence the biosynthetic capability of heterologous pathways.

Figure 14:
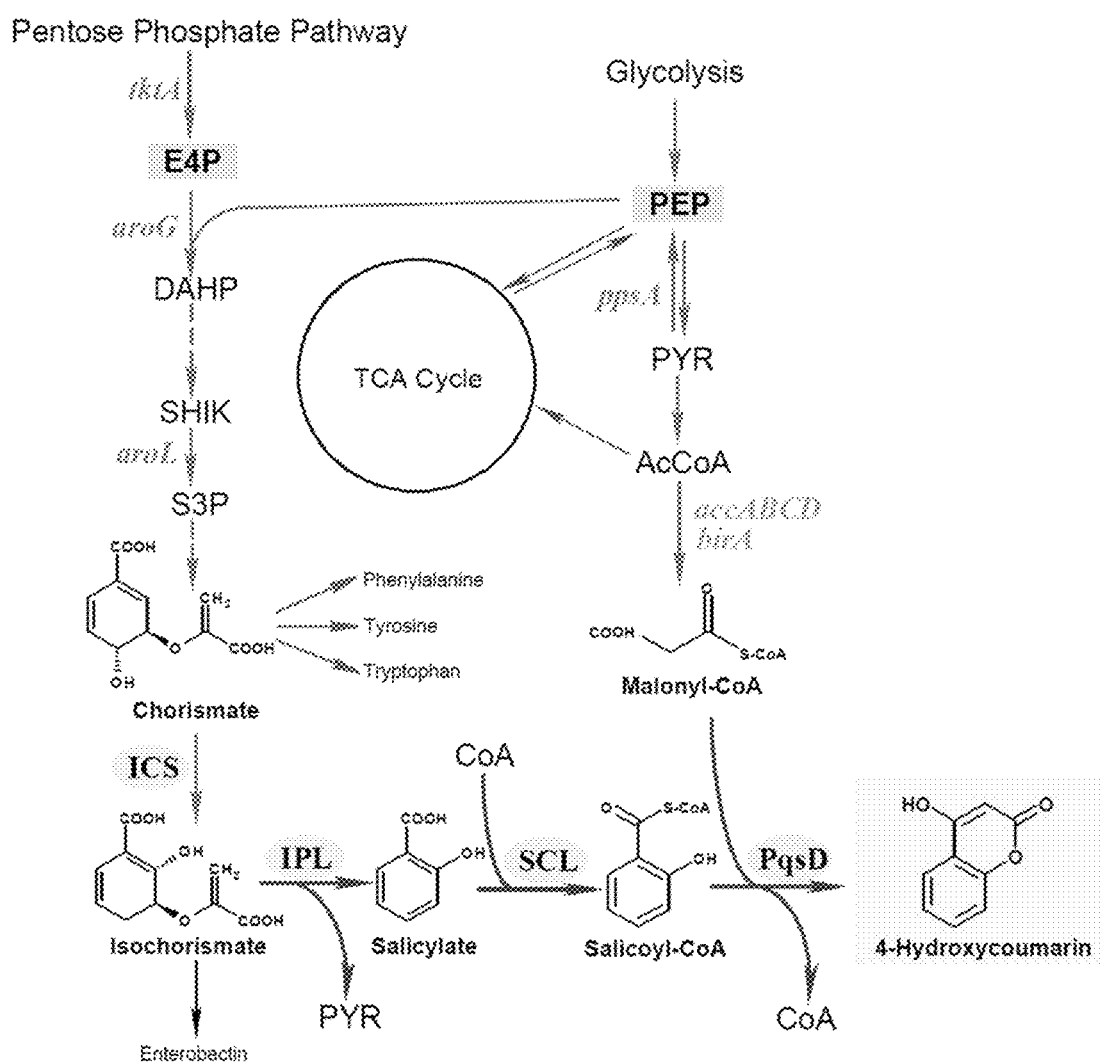
FIG. 14. Artificial 4HC biosynthetic mechanism shunted from shikimate pathway. E4P: D-erythrose-4-phosphate; PEP: phosphoenolpyruvate; PYR: pyruvate; AcCOA: acetyl-CoA; DAHP: 3-deoxy-D-arabino-heptulosonate-7-phosphate; SHIK: shikimate; S3P: shikimate-3-phosphate.

We further speculated that boosting the availability of chorismate and/or malonyl-CoA, the two major intermediates of 4HC biosynthesis, may divert more metabolic flux towards product formation. Chorismate is an intermediate in the shikimate pathway, of which the rate-limiting steps have been identified and the regulation mechanism has been well studied. As shown in FIG. 14, the 3-deoxy-D-arabino-heptulosonate-7-phosphate synthases (DAHPS) in *E. coli* encoded by aroG, aroF, and aroH are feedback-inhibited by phenylalanine, tyrosine, and tryptophan, respectively (Kikuchi et al. *Appl. Environ. Microbiol.* 63, 761-762 (1997). Moreover, the erythrose-4-phosphate (E4P) and phosphoenolpyruvate (PEP) availability limit can be alleviated by over-expressing transketolase (encoded by tktA) and PEP synthase (encoded by ppsA), respectively (Lutke-Eversloh et al. *Appl. Microbiol. Biotechnol.* 75, 103-110 (2007)). Besides, shikimate kinase (encoded by aroK/aroL) was proved to be another bottleneck which can be eliminated by the over-expression of aroL (Luetke-Eversloh et al. *Metab. Eng.* 10, 69-77 (2008)). Based on this knowledge, we cloned aroL, ppsA, tktA, and the feedback-inhibition-resistant aroG (aroG$^{fbr}$) into pCS27 generating a chorismate-boosting plasmid pCS-APTA. The *E. coli* strain carrying pZE-EPPS and pCS-APTA (Strain E, FIG. 13E) produced 283.9 mg/L 4HC in 18 h, a 37% increase compared with its parent Strain C. Meanwhile, we created another construct by inserting $P_L$lacO1-APTA operon into pZE-EP generating a dual-operon plasmid pZE-EP-APTA, which was co-transferred together with pCS-PS into *E. coli* (Strain D, FIG. 13D). Remarkably, Strain D produced 483.1 mg/L 4HC in 24 h, reflecting 4.4- and 11.4-fold increases compared with its parent (Strain B) and Strain A, respectively. Meanwhile, we detected the accumulation of salicylate at the concentrations of 197.6 and 222.3 mg/L at 24 h for Strains D and E, respectively, due to the boosting of shikimate pathway.

Furthermore, we examined the impact of malonyl-CoA on the production of 4HC. Since it has been reported that over-expression of acetyl-CoA carboxylase (accABCD) and biotin ligase (birA) can increase the availability of malonyl-CoA (Leonard et al. *Appl. Environ. Microbiol.* 73, 3877-3886 (2007)), (Zha et al. *Metab. Eng.* 11, 192-198 (2009)), we cloned genes accADBC and birA into pSA74 generating a malonyl-CoA-enhancing plasmid pSA-ACCB. The introduction of pSA-ACCB into Strain E led to slightly improved production of 4HC (313.4 mg/L, 11% higher than Strain E). However, the pSA-ACCB exerted negative influence to Strain D (*E. coli*/pZE-EP-APTA and pCS-PS), manifesting a dramatic fall in the 4HC production (184.1 mg/L). The results indicated that: 1) malonyl-CoA availability might not be a dominant limiting factor in 4HC production; 2) the over-expression of accADBC and birA could improve malonyl-CoA availability but might cause metabolic burden in strain D, which offset their benefit in boosting malonyl-CoA availability.

Semi-Synthesis of Warfarin.

Figure 15:
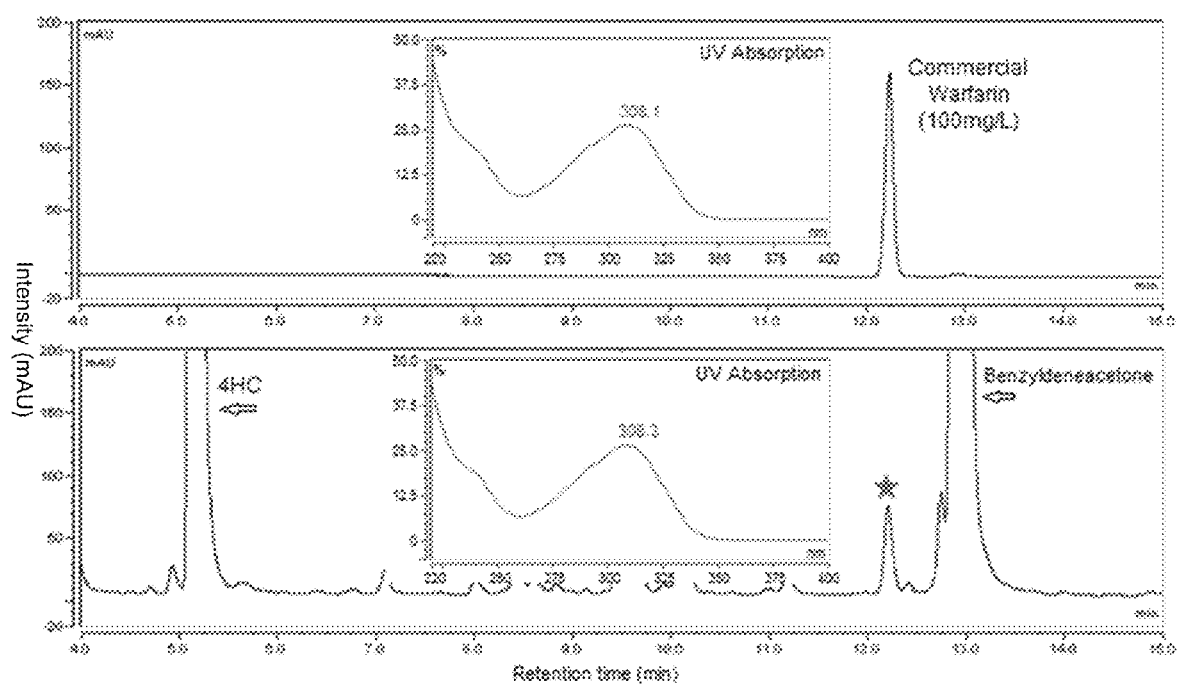
FIG. 15. HPLC analysis of the standard and semi-synthesized warfarin. The red-colored asterisk indicates the peak of the semi-synthesized warfarin. Its retention time was about 12.2 min. UV absorption profiles are shown beside the warfarin peaks. The peaks of the precursors 4HC and benzyldeneacetone were also indicated.

With tentative optimization, the resulting *E. coli* strain demonstrated great scale-up potential for 4HC production. Then we explored the feasibility of in situ semi-synthesis of warfarin via a green chemistry approach (Rogozinska et al. *Green Chem.* 13, 1155-1157 (2011)). To this end, the other precursor benzyldeneacetone and the catalyst (S,S)-1,2-diphenylethylenediamine were added into the supernatant of the strain D culture (containing about 500 mg/L 4HC) and incubated in a sonication bath for 3 hours. Quantitative HPLC analysis indicated that 43.7±2.6 mg/L warfarin was generated in the supernatant corresponding to a molar yield of 4.6% (FIG. 15). The low yield might be due to the facts that: 1) the aqueous condition is not optimal for the Michael addition reaction; 2) 4HC concentration is lower than the optimal concentration for warfarin synthesis.

Discussion

Recent advances of metabolic engineering have allowed microorganisms to be engineered to enable the efficient and environmental-friendly production of valuable molecules. Although the design principles for constituting a productive pathway are explored and yet to be well-established, recruitment of catalytically superior and host-suitable enzymes should be the primary one in the principles, which is evidenced by this work and previous studies (Atsumi et al. *Nature* 451, 86-89 (2008)), (Bond-Watts et al. *Nat. Chem. Biol.* 7, 222-227 (2011)), (Shen et al. *Appl. Environ. Microbiol.* 77, 2905-2915 (2011). Conventionally, sequence-based bioprospecting aided by bioinformatics and computational tools is an effective approach in searching for such candidates. For instance, BLAST search using the sequence information of an enzyme with known function as a query may be employed to identify homologous enzymes from various organisms capable of catalyzing the same type of reaction but exhibiting enhanced activity and desired substrate specificity (Dhamankar et al. *Curr. Opin. Struct. Biol.* 21, 488-494 (2011)). In our work, we first developed an in vitro complementation assay to accurately locate the rate-limiting step in the 4HC biosynthesis. To eliminate the bottleneck, we further employed a function-based bioprospecting strategy to search for a more suitable enzyme. We successfully identified 4-hydroxy-2(1H)-quinolone synthase for efficient microbial biosynthesis of 4HC totally based on the similarity in catalytic mechanisms and substrate/product structures between BIS and 4-hydroxy-2(1H)-quinolone synthase. Indeed, 4-hydroxy-2(1H)-quinolone synthase shares low sequence identity with BIS (around 25%), but exhibits functional and catalytic attributes of both CHS and FabH-like enzymes. On one hand, it can catalyze the condensation of malonyl-CoA as well as intra-molecular cyclization, which are the properties of CHS-like PKS; on the other hand, it can also condense malonyl-ACP in a manner of FabH (Bera et al. *Biochemistry (Mosc.)* 48, 8644-8655 (2009)). So far, the function-based bioprospecting can only be performed manually through analyzing and comparing enzyme catalytic mechanisms. However, we envision the development of computational tools that can effectively predict the catalytic substitutability of enzymes with low sequence correlation will further enhance our capability of engineering combinatorial biosynthesis.

With efficient enzymes available for each catalytic step, optimization of the pathway by adjusting expression level of individual enzymes is also critical for the pathway's overall performance. First, inharmonious expression of pathway enzymes may waste cellular resources for the formation of unnecessary RNAs, proteins, or intermediates. Besides, over-expression of some exotic enzymes is stressful or toxic to host cells, which may result in growth retardation and undesired adaptive responses, hence reducing yield and productivity (Zhang et al. *Nat. Biotechnol.* 30, 354-359 (2012)). Methodologies have been developed to determine the ideal expression level and have been successfully applied by fine-tuning the expression level of pathway enzymes and modules, such as the use of plasmids with different copy numbers, promoters with various transcription strengths, and synthetic RBSs with different translation efficiencies (Ajikumar et al. *Science* 330, 70-74 (2010)), (Salis et al. *Nat. Biotechnol.* 27, 946-950 (2009), (Xu et al. *Nat. Commun.* 4, 1409 (2013)), (Anthony et al. *Metab. Eng.* 11, 13-19 (2009)). In our case, modular optimization by adjusting gene organization, copy number, and operon configuration also led to around 5-fold increase in the 4HC titer (Strain C vs. Strain A).

In conclusion, this work achieves microbial production of the pharmaceutically important drug precursor 4HC for the first time and demonstrates great scale-up potential. The findings provide a new insight into the non-natural 4HC biosynthesis, which can serve as a starting point for expanding the molecular diversity of coumarin compounds through synthetic chemistry and biology approaches.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A genetically engineered microbe that comprises a metabolic pathway for the production of 4-hydroxycoumarin from a chorismate intermediate, wherein the metabolic pathway comprises a salicylate:CoA ligase and an enzyme catalyzing the condensation of a salicoyl-CoA and a malonyl-CoA to form 4-hydroxycoumarin.

2. The microbe of claim 1 wherein the microbe is *E. coli*.

3. The microbe of claim 1 wherein the microbe expresses an isochorismate synthase.

4. The microbe of claim 1 wherein the microbe expresses an isochorismate pyruvate lyase.

5. The microbe of claim 1 wherein the enzyme catalyzing the condensation of a salicoyl-CoA and a malonyl-CoA to form 4-hydroxycoumarin is a *Pseudomonas* quinolone synthase (PqsD).

6. The microbe of claim 1 wherein at least one enzyme of the metabolic pathway is exogenous with respect to the microbe.

7. The microbe of claim 6 comprising a first plasmid comprising a polynucleotide encoding the at least one enzyme of the metabolic pathway, the enzyme selected from isochorismate synthase, isochorismate pyruvate lyase, salicylate:CoA ligase, and a *Pseudomonas* quinolone synthase (PqsD).

8. The microbe of claim 6 comprising a first plasmid comprising a polynucleotide encoding an isochorismate synthase and an isochorismate pyruvate lyase, and the microbe further comprising second plasmid comprising a polynucleotide encoding a salicylate:CoA ligase and a *Pseudomonas* quinolone synthase (PqsD).

9. The microbe of claim 1 further comprising increased production of chorismate compared to a control cell.

10. The microbe of claim 9 wherein the microbe expresses a feedback inhibition resistant 3-deoxy-D-arabino-heptulosonate-7-phosphate synthase.

11. The microbe of claim 10 wherein the feedback inhibition resistant 3-deoxy-D-arabino-heptulosonate-7-phosphate synthase is encoded by aroG.

12. The microbe of claim 9 wherein the microbe expresses a phosphoenolpyruvate synthase at an increased level compared to a control cell.

13. The microbe of claim 9 wherein the microbe expresses a transketolase at an increased level compared to a control cell.

14. The microbe of claim 9 wherein the microbe expresses a shikimate kinase at an increased level compared to a control cell.

15. A method comprising:
   culturing the genetically engineered microbe of claim 1 under conditions suitable for the production of 4-hydroxycoumarin, wherein 4-hydroxycoumarin is produced.

16. The method of claim 15 further comprising enriching the 4-hydroxycoumarin produced during the culturing.

17. The method of claim 16 wherein the enriching comprises removing the cells from the culture.

18. The method of claim 15 wherein the 4-hydroxycoumarin is isolated.

19. The method of claim 15 further comprising adding benzyldeneacetone and (S,S)-1,2-diphenylethylenediamine to convert the 4-hydroxycoumarin to warfarin.

* * * * *

SEQUENCE LISTING

```
<160> NUMBER OF SEQ ID NOS: 58

<210> SEQ ID NO 1
<211> LENGTH: 391
<212> TYPE: PRT
<213> ORGANISM: Escherichia coli

<400> SEQUENCE: 1

Met Asp Thr Ser Leu Ala Glu Glu Val Gln Gln Thr Met Ala Thr Leu
1               5                   10                  15

Ala Pro Asn Arg Phe Phe Phe Met Ser Pro Tyr Arg Ser Phe Thr Thr
            20                  25                  30

Ser Gly Cys Phe Ala Arg Phe Asp Glu Pro Ala Val Asn Gly Asp Ser
        35                  40                  45

Pro Asp Ser Pro Phe Gln Gln Lys Leu Ala Ala Leu Phe Ala Asp Ala
    50                  55                  60

Lys Ala Gln Gly Ile Lys Asn Pro Val Met Val Gly Ala Ile Pro Phe
65                  70                  75                  80

Asp Pro Arg Gln Pro Ser Ser Leu Tyr Ile Pro Glu Ser Trp Gln Ser
                85                  90                  95

Phe Ser Arg Gln Glu Lys Gln Ala Ser Ala Arg Arg Phe Thr Arg Ser
            100                 105                 110

Gln Ser Leu Asn Val Val Glu Arg Gln Ala Ile Pro Glu Gln Thr Thr
        115                 120                 125

Phe Glu Gln Met Val Ala Arg Ala Ala Ala Leu Thr Ala Thr Pro Gln
    130                 135                 140

Val Asp Lys Val Val Leu Ser Arg Leu Ile Asp Ile Thr Thr Asp Ala
145                 150                 155                 160

Ala Ile Asp Ser Gly Val Leu Leu Glu Arg Leu Ile Ala Gln Asn Pro
                165                 170                 175

Val Ser Tyr Asn Phe His Val Pro Leu Ala Asp Gly Gly Val Leu Leu
            180                 185                 190

Gly Ala Ser Pro Glu Leu Leu Leu Arg Lys Asp Gly Glu Arg Phe Ser
        195                 200                 205

Ser Ile Pro Leu Ala Gly Ser Ala Arg Arg Gln Pro Asp Glu Val Leu
```

```
                    210                 215                 220
Asp Arg Glu Ala Gly Asn Arg Leu Leu Ala Ser Glu Lys Asp Arg His
225                 230                 235                 240

Glu His Glu Leu Val Thr Gln Ala Met Lys Glu Val Leu Arg Glu Arg
                    245                 250                 255

Ser Ser Glu Leu His Val Pro Ser Pro Gln Leu Ile Thr Thr Pro
                    260                 265                 270

Thr Leu Trp His Leu Ala Thr Pro Phe Glu Gly Lys Ala Asn Ser Gln
            275                 280                 285

Glu Asn Ala Leu Thr Leu Ala Cys Leu Leu His Pro Thr Pro Ala Leu
290                 295                 300

Ser Gly Phe Pro His Gln Ala Ala Thr Gln Val Ile Ala Glu Leu Glu
305                 310                 315                 320

Pro Phe Asp Arg Glu Leu Phe Gly Gly Ile Val Gly Trp Cys Asp Ser
                    325                 330                 335

Glu Gly Asn Gly Glu Trp Val Val Thr Ile Arg Cys Ala Lys Leu Arg
                    340                 345                 350

Glu Asn Gln Val Arg Leu Phe Ala Gly Ala Gly Ile Val Pro Ala Ser
            355                 360                 365

Ser Pro Leu Gly Glu Trp Arg Glu Thr Gly Val Lys Leu Ser Thr Met
370                 375                 380

Leu Asn Val Phe Gly Leu His
385                 390

<210> SEQ ID NO 2
<211> LENGTH: 101
<212> TYPE: PRT
<213> ORGANISM: Pseudomonas aeruginosa

<400> SEQUENCE: 2

Met Lys Thr Pro Glu Asp Cys Thr Gly Leu Ala Asp Ile Arg Glu Ala
1               5                   10                  15

Ile Asp Arg Ile Asp Leu Asp Ile Val Gln Ala Leu Gly Arg Arg Met
                20                  25                  30

Asp Tyr Val Lys Ala Ala Ser Arg Phe Lys Ala Ser Glu Ala Ala Ile
            35                  40                  45

Pro Ala Pro Glu Arg Val Ala Ala Met Leu Pro Glu Arg Ala Arg Trp
        50                  55                  60

Ala Glu Glu Asn Gly Leu Asp Ala Pro Phe Val Glu Gly Leu Phe Ala
65                  70                  75                  80

Gln Ile Ile His Trp Tyr Ile Ala Glu Gln Ile Lys Tyr Trp Arg Gln
                85                  90                  95

Thr Arg Gly Ala Ala
            100

<210> SEQ ID NO 3
<211> LENGTH: 553
<212> TYPE: PRT
<213> ORGANISM: Streptomyces sp. WA46

<400> SEQUENCE: 3

Met Thr Arg Glu Gly Phe Val Pro Trp Pro Lys Glu Ala Ala Asp Arg
1               5                   10                  15

Tyr Arg Glu Ala Gly Tyr Trp Arg Gly Arg Pro Leu Gly Ser Tyr Leu
                20                  25                  30

His Glu Trp Ala Glu Thr Tyr Gly Asp Thr Val Ala Val Val Asp Gly
```

```
                35                  40                  45
Asp Thr Arg Leu Thr Tyr Arg Gln Leu Val Asp Arg Ala Asp Gly Leu
                50                  55                  60
Ala Cys Arg Leu Leu Asp Ser Gly Leu Asn Pro Gly Asp Ala Met Leu
 65                  70                  75                  80
Val Gln Leu Pro Asn Gly Trp Glu Phe Val Thr Leu Thr Leu Ala Cys
                    85                  90                  95
Leu Arg Ala Gly Ile Ala Pro Val Met Ala Met Pro Ala His Arg Gly
                100                 105                 110
His Glu Leu Arg Tyr Leu Ala Ala His Ala Glu Val Thr Ser Ile Ala
                115                 120                 125
Val Pro Asp Arg Leu Gly Asp Phe Asp His Gln Ala Leu Gly Arg Glu
                130                 135                 140
Val Ala Glu Asp Thr Pro Ser Val Gly Leu Leu Val Ala Gly Gly
145                 150                 155                 160
Thr Val Gly Thr Asp Ala Thr Asp Leu Arg Ala Leu Ala Glu Pro Ala
                    165                 170                 175
Asp Asp Pro Val Thr Ala Arg Ala Arg Leu Asp Arg Ile Ala Pro Asp
                180                 185                 190
Ser Gly Asp Ile Ala Val Phe Leu Leu Ser Gly Gly Thr Gly Leu
                195                 200                 205
Pro Lys Leu Ile Thr Arg Thr His Asp Asp Tyr Glu Tyr Asn Ala Arg
210                 215                 220
Arg Ser Ala Glu Val Cys Gly Leu Asp Ser Asp Ser Val Tyr Leu Val
225                 230                 235                 240
Ala Leu Pro Ala Gly His Asn Phe Pro Leu Ala Cys Pro Gly Ile Leu
                    245                 250                 255
Gly Thr Leu Met Asn Gly Gly Arg Val Val Leu Ala Arg Thr Pro Glu
                260                 265                 270
Pro Gly Lys Val Leu Pro Leu Met Ala Ala Glu Gly Val Thr Ala Thr
                275                 280                 285
Ala Ala Val Pro Ala Val Val Gln Arg Trp Ile Asp Ala Val Ala Ser
                290                 295                 300
Gly Arg His Pro Ala Pro Pro Ala Leu Arg Leu Leu Gln Val Gly Gly
305                 310                 315                 320
Ala Arg Leu Ala Pro Glu Val Ala Arg Ala Glu Pro Val Leu Gly
                    325                 330                 335
Gly Thr Leu Gln Gln Val Phe Gly Met Ala Glu Gly Leu Leu Asn Tyr
                340                 345                 350
Thr Arg Pro Asp Asp Pro Asp Asp Ile Lys Ile Glu Thr Gln Gly Arg
                355                 360                 365
Pro Met Cys Pro Asp Asp Glu Ile Leu Val Val Asp Ala Ser Asp Asn
                370                 375                 380
Pro Val Pro Pro Gly Glu Met Gly Ala Leu Leu Thr Arg Gly Pro Tyr
385                 390                 395                 400
Thr Pro Arg Gly Tyr Tyr Arg Ala Ala Glu His Asn Ala Arg Ala Phe
                    405                 410                 415
Thr Pro Asp Gly Trp Tyr Arg Thr Gly Asp Val Val Arg Leu His Pro
                420                 425                 430
Ser Gly Asn Leu Val Val Glu Gly Arg Asp Lys Asp Leu Ile Asn Arg
                435                 440                 445
Gly Gly Glu Lys Ile Ser Ala Glu Glu Val Glu Asn Leu Ile Tyr Arg
                450                 455                 460
```

```
Leu Pro Gly Val Ala Arg Val Ala Val Ala Lys Ala Asp Pro Asp
465                 470                 475                 480

Leu Gly Glu Arg Val Cys Ala Val Val Val Glu Pro Gly Thr Gln
                485                 490                 495

Leu Ser Leu Glu Ser Val Arg Ala Ala Leu Thr Ala Met Gln Val Ala
            500                 505                 510

Arg Tyr Lys Leu Pro Glu Asp Leu Val Val Asp Glu Leu Pro Leu
            515                 520                 525

Thr Lys Val Gly Lys Ile Asp Lys Lys Arg Leu Arg Asp Val Val Arg
530                 535                 540

Gly Lys Ala Asp Ser Val Glu Ala Val
545                 550

<210> SEQ ID NO 4
<211> LENGTH: 337
<212> TYPE: PRT
<213> ORGANISM: Pseudomonas aeruginosa

<400> SEQUENCE: 4

Met Gly Asn Pro Ile Leu Ala Gly Leu Gly Phe Ser Leu Pro Lys Arg
1               5                   10                  15

Gln Val Ser Asn His Asp Leu Val Gly Arg Ile Asn Thr Ser Asp Glu
            20                  25                  30

Phe Ile Val Glu Arg Thr Gly Val Arg Thr Arg Tyr His Val Glu Pro
        35                  40                  45

Glu Gln Ala Val Ser Ala Leu Met Val Pro Ala Ala Arg Gln Ala Ile
    50                  55                  60

Glu Ala Ala Gly Leu Leu Pro Glu Asp Ile Asp Leu Leu Val Asn
65                  70                  75                  80

Thr Leu Ser Pro Asp His His Asp Pro Ser Gln Ala Cys Leu Ile Gln
                85                  90                  95

Pro Leu Leu Gly Leu Arg His Ile Pro Val Leu Asp Ile Arg Ala Gln
            100                 105                 110

Cys Ser Gly Leu Leu Tyr Gly Leu Gln Met Ala Arg Gly Gln Ile Leu
        115                 120                 125

Ala Gly Leu Ala Arg His Val Leu Val Val Cys Gly Glu Val Leu Ser
    130                 135                 140

Lys Arg Met Asp Cys Ser Asp Arg Gly Arg Asn Leu Ser Ile Leu Leu
145                 150                 155                 160

Gly Asp Gly Ala Gly Ala Val Val Ser Ala Gly Glu Ser Leu Glu
                165                 170                 175

Asp Gly Leu Leu Asp Leu Arg Leu Gly Ala Asp Gly Asn Tyr Phe Asp
            180                 185                 190

Leu Leu Met Thr Ala Ala Pro Gly Ser Ala Ser Pro Thr Phe Leu Asp
        195                 200                 205

Glu Asn Val Leu Arg Glu Gly Gly Glu Phe Leu Met Arg Gly Arg
    210                 215                 220

Pro Met Phe Glu His Ala Ser Gln Thr Leu Val Arg Ile Ala Gly Glu
225                 230                 235                 240

Met Leu Ala Ala His Glu Leu Thr Leu Asp Asp Ile Asp His Val Ile
                245                 250                 255

Cys His Gln Pro Asn Leu Arg Ile Leu Asp Ala Val Gln Glu Gln Leu
            260                 265                 270

Gly Ile Pro Gln His Lys Phe Ala Val Thr Val Asp Arg Leu Gly Asn
```

```
            275                 280                 285
Met Ala Ser Ala Ser Thr Pro Val Thr Leu Ala Met Phe Trp Pro Asp
    290                 295                 300

Ile Gln Pro Gly Gln Arg Val Leu Val Leu Thr Tyr Gly Ser Gly Ala
305                 310                 315                 320

Thr Trp Gly Ala Ala Leu Tyr Arg Lys Pro Glu Glu Val Asn Arg Pro
                325                 330                 335

Cys
```

<210> SEQ ID NO 5
<211> LENGTH: 38
<212> TYPE: DNA
<213> ORGANISM: artificial
<220> FEATURE:
<223> OTHER INFORMATION: synthetic oligonucleotide primer

<400> SEQUENCE: 5
gggaaaggat ccggatacgt cactggctga ggaagtac                    38

<210> SEQ ID NO 6
<211> LENGTH: 44
<212> TYPE: DNA
<213> ORGANISM: artificial
<220> FEATURE:
<223> OTHER INFORMATION: synthetic oligonucleotide primer

<400> SEQUENCE: 6
gggaaactgc agttaatgca atccaaaaac gttcaacatg gtag             44

<210> SEQ ID NO 7
<211> LENGTH: 35
<212> TYPE: DNA
<213> ORGANISM: artificial
<220> FEATURE:
<223> OTHER INFORMATION: synthetic oligonucleotide primer

<400> SEQUENCE: 7
gggaaaggat ccgcaatcac ttactacggc gctgg                       35

<210> SEQ ID NO 8
<211> LENGTH: 42
<212> TYPE: DNA
<213> ORGANISM: artificial
<220> FEATURE:
<223> OTHER INFORMATION: synthetic oligonucleotide primer

<400> SEQUENCE: 8
gggaaactgc agctattcca tttgtaataa agtacgcagc cc               42

<210> SEQ ID NO 9
<211> LENGTH: 38
<212> TYPE: DNA
<213> ORGANISM: artificial
<220> FEATURE:
<223> OTHER INFORMATION: synthetic oligonucleotide primer

<400> SEQUENCE: 9
gggaaaggat ccgagccggc tggcgcccct gagccagt                    38

<210> SEQ ID NO 10
<211> LENGTH: 33
<212> TYPE: DNA
<213> ORGANISM: artificial
<220> FEATURE:

<223> OTHER INFORMATION: synthetic oligonucleotide primer

<400> SEQUENCE: 10
gggaaagtcg actcaggcga cgccgcgctg caa                33

<210> SEQ ID NO 11
<211> LENGTH: 34
<212> TYPE: DNA
<213> ORGANISM: artificial
<220> FEATURE:
<223> OTHER INFORMATION: synthetic oligonucleotide primer

<400> SEQUENCE: 11
gggaaaggat ccgaaaactc ccgaagactg cacc               34

<210> SEQ ID NO 12
<211> LENGTH: 32
<212> TYPE: DNA
<213> ORGANISM: artificial
<220> FEATURE:
<223> OTHER INFORMATION: synthetic oligonucleotide primer

<400> SEQUENCE: 12
gggaaactgc agtcatgcgg caccccgtgt ct                 32

<210> SEQ ID NO 13
<211> LENGTH: 35
<212> TYPE: DNA
<213> ORGANISM: artificial
<220> FEATURE:
<223> OTHER INFORMATION: synthetic oligonucleotide primer

<400> SEQUENCE: 13
gggaaaggat ccgctggcct tcgacccat gaatt               35

<210> SEQ ID NO 14
<211> LENGTH: 36
<212> TYPE: DNA
<213> ORGANISM: artificial
<220> FEATURE:
<223> OTHER INFORMATION: synthetic oligonucleotide primer

<400> SEQUENCE: 14
gggaaactgc agtcactcat cttgggctcc ttgatc             36

<210> SEQ ID NO 15
<211> LENGTH: 35
<212> TYPE: DNA
<213> ORGANISM: artificial
<220> FEATURE:
<223> OTHER INFORMATION: synthetic oligonucleotide primer

<400> SEQUENCE: 15
gggaaaggat ccgacgcgtg agggattcgt gccct              35

<210> SEQ ID NO 16
<211> LENGTH: 34
<212> TYPE: DNA
<213> ORGANISM: artificial
<220> FEATURE:
<223> OTHER INFORMATION: synthetic oligonucleotide primer

<400> SEQUENCE: 16
gggaaactgc agtcacaccg cctcgacgga gtct               34

```
<210> SEQ ID NO 17
<211> LENGTH: 35
<212> TYPE: DNA
<213> ORGANISM: artificial
<220> FEATURE:
<223> OTHER INFORMATION: synthetic oligonucleotide primer

<400> SEQUENCE: 17
gggaaaggat ccgaccagca ttccgcgcat gatcc                              35

<210> SEQ ID NO 18
<211> LENGTH: 38
<212> TYPE: DNA
<213> ORGANISM: artificial
<220> FEATURE:
<223> OTHER INFORMATION: synthetic oligonucleotide primer

<400> SEQUENCE: 18
gggaaaaagc tttcagcggg tcggggcggt gacgaggt                           38

<210> SEQ ID NO 19
<211> LENGTH: 37
<212> TYPE: DNA
<213> ORGANISM: artificial
<220> FEATURE:
<223> OTHER INFORMATION: synthetic oligonucleotide primer

<400> SEQUENCE: 19
gggaaaggat ccggcccctg tggtcaagaa cgagcct                            37

<210> SEQ ID NO 20
<211> LENGTH: 36
<212> TYPE: DNA
<213> ORGANISM: artificial
<220> FEATURE:
<223> OTHER INFORMATION: synthetic oligonucleotide primer

<400> SEQUENCE: 20
gggaaactgc agtcagtagg tgatgaactc gctacg                             36

<210> SEQ ID NO 21
<211> LENGTH: 34
<212> TYPE: DNA
<213> ORGANISM: artificial
<220> FEATURE:
<223> OTHER INFORMATION: synthetic oligonucleotide primer

<400> SEQUENCE: 21
gggaaaggta ccatggcccc tgtggtcaag aacg                               34

<210> SEQ ID NO 22
<211> LENGTH: 39
<212> TYPE: DNA
<213> ORGANISM: artificial
<220> FEATURE:
<223> OTHER INFORMATION: synthetic oligonucleotide primer

<400> SEQUENCE: 22
gggaaacata tgtcagtagg tgatgaactc gctacgcag                          39

<210> SEQ ID NO 23
<211> LENGTH: 46
<212> TYPE: DNA
<213> ORGANISM: artificial
<220> FEATURE:
<223> OTHER INFORMATION: synthetic oligonucleotide primer
```

<400> SEQUENCE: 23
gggaaacata tgaggagata taccatgacg cgtgagggat tcgtgc    46

<210> SEQ ID NO 24
<211> LENGTH: 33
<212> TYPE: DNA
<213> ORGANISM: artificial
<220> FEATURE:
<223> OTHER INFORMATION: synthetic oligonucleotide primer

<400> SEQUENCE: 24
gggaaatcta gatcacaccg cctcgacgga gtc    33

<210> SEQ ID NO 25
<211> LENGTH: 40
<212> TYPE: DNA
<213> ORGANISM: artificial
<220> FEATURE:
<223> OTHER INFORMATION: synthetic oligonucleotide primer

<400> SEQUENCE: 25
gggaaaggta ccatggatac gtcactggct gaggaagtac    40

<210> SEQ ID NO 26
<211> LENGTH: 44
<212> TYPE: DNA
<213> ORGANISM: artificial
<220> FEATURE:
<223> OTHER INFORMATION: synthetic oligonucleotide primer

<400> SEQUENCE: 26
gggaaacata tgttaatgca atccaaaaac gttcaacatg gtag    44

<210> SEQ ID NO 27
<211> LENGTH: 45
<212> TYPE: DNA
<213> ORGANISM: artificial
<220> FEATURE:
<223> OTHER INFORMATION: synthetic oligonucleotide primer

<400> SEQUENCE: 27
gggaaacata tgaggagata taccatgctg gccttcgacc ccatg    45

<210> SEQ ID NO 28
<211> LENGTH: 39
<212> TYPE: DNA
<213> ORGANISM: artificial
<220> FEATURE:
<223> OTHER INFORMATION: synthetic oligonucleotide primer

<400> SEQUENCE: 28
gggaaagcat gctcactcat cttgggctcc ttgatccag    39

<210> SEQ ID NO 29
<211> LENGTH: 46
<212> TYPE: DNA
<213> ORGANISM: artificial
<220> FEATURE:
<223> OTHER INFORMATION: synthetic oligonucleotide primer

<400> SEQUENCE: 29
gggaaagcat gcaggagata taccatggcc cctgtggtca agaacg    46

<210> SEQ ID NO 30
<211> LENGTH: 39

```
<212> TYPE: DNA
<213> ORGANISM: artificial
<220> FEATURE:
<223> OTHER INFORMATION: synthetic oligonucleotide primer

<400> SEQUENCE: 30
gggaaacata tgtcagtagg tgatgaactc gctacgcag                    39

<210> SEQ ID NO 31
<211> LENGTH: 34
<212> TYPE: DNA
<213> ORGANISM: artificial
<220> FEATURE:
<223> OTHER INFORMATION: synthetic oligonucleotide primer

<400> SEQUENCE: 31
gggaaaggta ccatgggtaa tccgatcctg gccg                         34

<210> SEQ ID NO 32
<211> LENGTH: 33
<212> TYPE: DNA
<213> ORGANISM: artificial
<220> FEATURE:
<223> OTHER INFORMATION: synthetic oligonucleotide primer

<400> SEQUENCE: 32
gggaaacata tgtcaacatg gccggttcac ctc                          33

<210> SEQ ID NO 33
<211> LENGTH: 25
<212> TYPE: DNA
<213> ORGANISM: artificial
<220> FEATURE:
<223> OTHER INFORMATION: synthetic oligonucleotide primer

<400> SEQUENCE: 33
aaggcggtaa tacggttatc cacag                                   25

<210> SEQ ID NO 34
<211> LENGTH: 22
<212> TYPE: DNA
<213> ORGANISM: artificial
<220> FEATURE:
<223> OTHER INFORMATION: synthetic oligonucleotide primer

<400> SEQUENCE: 34
tgagtgagct gataccgctc gc                                      22

<210> SEQ ID NO 35
<211> LENGTH: 44
<212> TYPE: DNA
<213> ORGANISM: artificial
<220> FEATURE:
<223> OTHER INFORMATION: synthetic oligonucleotide primer

<400> SEQUENCE: 35
gcgagcggta tcagctcact caaggcgtat cacgaggccc tttc              44

<210> SEQ ID NO 36
<211> LENGTH: 47
<212> TYPE: DNA
<213> ORGANISM: artificial
<220> FEATURE:
<223> OTHER INFORMATION: synthetic oligonucleotide primer

<400> SEQUENCE: 36
```

```
ctgtggataa ccgtattacc gcctttaggg cggcggattt gtcctac          47
```

<210> SEQ ID NO 37
<211> LENGTH: 46
<212> TYPE: DNA
<213> ORGANISM: artificial
<220> FEATURE:
<223> OTHER INFORMATION: synthetic oligonucleotide primer

<400> SEQUENCE: 37

```
gggaaacata tgaggagata taccatgacg cgtgagggat tcgtgc           46
```

<210> SEQ ID NO 38
<211> LENGTH: 33
<212> TYPE: DNA
<213> ORGANISM: artificial
<220> FEATURE:
<223> OTHER INFORMATION: synthetic oligonucleotide primer

<400> SEQUENCE: 38

```
gggaaaggat cctcacaccg cctcgacgga gtc                         33
```

<210> SEQ ID NO 39
<211> LENGTH: 46
<212> TYPE: DNA
<213> ORGANISM: artificial
<220> FEATURE:
<223> OTHER INFORMATION: synthetic oligonucleotide primer

<400> SEQUENCE: 39

```
gggaaagcat gcaggagata taccatgggt aatccgatcc tggccg           46
```

<210> SEQ ID NO 40
<211> LENGTH: 33
<212> TYPE: DNA
<213> ORGANISM: artificial
<220> FEATURE:
<223> OTHER INFORMATION: synthetic oligonucleotide primer

<400> SEQUENCE: 40

```
gggaaacata tgtcaacatg gccggttcac ctc                         33
```

<210> SEQ ID NO 41
<211> LENGTH: 40
<212> TYPE: DNA
<213> ORGANISM: artificial
<220> FEATURE:
<223> OTHER INFORMATION: synthetic oligonucleotide primer

<400> SEQUENCE: 41

```
gggaaaggta ccatgacaca acctctttt ctgatcgggc                   40
```

<210> SEQ ID NO 42
<211> LENGTH: 39
<212> TYPE: DNA
<213> ORGANISM: artificial
<220> FEATURE:
<223> OTHER INFORMATION: synthetic oligonucleotide primer

<400> SEQUENCE: 42

```
gggaaacata tgtcaacaat tgatcgtctg tgccagggc                   39
```

<210> SEQ ID NO 43
<211> LENGTH: 46
<212> TYPE: DNA
<213> ORGANISM: artificial

<220> FEATURE:
<223> OTHER INFORMATION: synthetic oligonucleotide primer

<400> SEQUENCE: 43
gggaaacata tgaggagata taccatgtcc aacaatggct cgtcac        46

<210> SEQ ID NO 44
<211> LENGTH: 40
<212> TYPE: DNA
<213> ORGANISM: artificial
<220> FEATURE:
<223> OTHER INFORMATION: synthetic oligonucleotide primer

<400> SEQUENCE: 44
gggaaagtcg acttatttct tcagttcagc caggcttaac        40

<210> SEQ ID NO 45
<211> LENGTH: 48
<212> TYPE: DNA
<213> ORGANISM: artificial
<220> FEATURE:
<223> OTHER INFORMATION: synthetic oligonucleotide primer

<400> SEQUENCE: 45
gggaaactcg agaggagata taccatgtcc tcacgtaaag agcttgcc        48

<210> SEQ ID NO 46
<211> LENGTH: 39
<212> TYPE: DNA
<213> ORGANISM: artificial
<220> FEATURE:
<223> OTHER INFORMATION: synthetic oligonucleotide primer

<400> SEQUENCE: 46
gggaaagcat gcttacagca gttcttttgc tttcgcaac        39

<210> SEQ ID NO 47
<211> LENGTH: 51
<212> TYPE: DNA
<213> ORGANISM: artificial
<220> FEATURE:
<223> OTHER INFORMATION: synthetic oligonucleotide primer

<400> SEQUENCE: 47
gggaaagcat gcaggagata taccatgaat tatcagaacg acgatttacg c        51

<210> SEQ ID NO 48
<211> LENGTH: 33
<212> TYPE: DNA
<213> ORGANISM: artificial
<220> FEATURE:
<223> OTHER INFORMATION: synthetic oligonucleotide primer

<400> SEQUENCE: 48
gggaaaaagc ttttacccgc gacgcgcttt tac        33

<210> SEQ ID NO 49
<211> LENGTH: 36
<212> TYPE: DNA
<213> ORGANISM: artificial
<220> FEATURE:
<223> OTHER INFORMATION: synthetic oligonucleotide primer

<400> SEQUENCE: 49
gggaaagagc tctcttcacc tcgagaattg tgagcg        36

<210> SEQ ID NO 50
<211> LENGTH: 34
<212> TYPE: DNA
<213> ORGANISM: artificial
<220> FEATURE:
<223> OTHER INFORMATION: synthetic oligonucleotide primer

<400> SEQUENCE: 50
gggaaaacta gtctactcag gagagcgttc accg                              34

<210> SEQ ID NO 51
<211> LENGTH: 43
<212> TYPE: DNA
<213> ORGANISM: artificial
<220> FEATURE:
<223> OTHER INFORMATION: synthetic oligonucleotide primer

<400> SEQUENCE: 51
gggaaaggta ccatgagtct gaatttcctt gattttgaac agc                    43

<210> SEQ ID NO 52
<211> LENGTH: 36
<212> TYPE: DNA
<213> ORGANISM: artificial
<220> FEATURE:
<223> OTHER INFORMATION: synthetic oligonucleotide primer

<400> SEQUENCE: 52
gggaaactgc agttacgcgt aaccgtagct catcag                            36

<210> SEQ ID NO 53
<211> LENGTH: 51
<212> TYPE: DNA
<213> ORGANISM: artificial
<220> FEATURE:
<223> OTHER INFORMATION: synthetic oligonucleotide primer

<400> SEQUENCE: 53
gggaaactgc agaggagata taccatgagc tggattgaac gaattaaaag c            51

<210> SEQ ID NO 54
<211> LENGTH: 33
<212> TYPE: DNA
<213> ORGANISM: artificial
<220> FEATURE:
<223> OTHER INFORMATION: synthetic oligonucleotide primer

<400> SEQUENCE: 54
gggaaagtcg actcaggcct caggttcctg atc                               33

<210> SEQ ID NO 55
<211> LENGTH: 57
<212> TYPE: DNA
<213> ORGANISM: artificial
<220> FEATURE:
<223> OTHER INFORMATION: synthetic oligonucleotide primer

<400> SEQUENCE: 55
gggaaagtcg acaggagata taccatggat attcgtaaga ttaaaaaact gatcgag     57

<210> SEQ ID NO 56
<211> LENGTH: 43
<212> TYPE: DNA
<213> ORGANISM: artificial
<220> FEATURE:
<223> OTHER INFORMATION: synthetic oligonucleotide primer

```
<400> SEQUENCE: 56
gggaaagaat tcttattttt cctgaagacc gagtttttc tcc                      43

<210> SEQ ID NO 57
<211> LENGTH: 46
<212> TYPE: DNA
<213> ORGANISM: artificial
<220> FEATURE:
<223> OTHER INFORMATION: synthetic oligonucleotide primer

<400> SEQUENCE: 57
gggaaagaat tcaggagata taccatgaag gataacaccg tgccac                  46

<210> SEQ ID NO 58
<211> LENGTH: 42
<212> TYPE: DNA
<213> ORGANISM: artificial
<220> FEATURE:
<223> OTHER INFORMATION: synthetic oligonucleotide primer

<400> SEQUENCE: 58
gggaaaggat ccttattttt ctgcactacg cagggatatt tc                      42
```